(12) United States Patent
Straub et al.

(10) Patent No.: US 6,451,805 B1
(45) Date of Patent: Sep. 17, 2002

(54) SUBSTITUTED PYRAZOLE DERIVATIVES FOR THE TREATMENT OF CARDIOCIRCULATORY DISEASES

(75) Inventors: Alexander Straub, Wuppertal; Chantal Fürstner, Ruhr; Thomas Jaetsch, Köln; Achim Feurer, Odenthal; Raimund Kast, Wuppertal; Johannes-Peter Stasch, Solingen; Elisabeth Perzborn; Joachim Hütter, both of Wuppertal; Klaus Dembowsky, Schriesheim, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/297,121

(22) PCT Filed: Nov. 14, 1997

(86) PCT No.: PCT/EP97/06366

§ 371 (c)(1),
(2), (4) Date: Apr. 23, 1999

(87) PCT Pub. No.: WO98/23619

PCT Pub. Date: Jun. 4, 1998

(51) Int. Cl.$^7$ .................... A61K 31/506; C07D 403/04
(52) U.S. Cl. ...................................... 514/269; 544/333
(58) Field of Search ........................... 514/269; 544/333

(56) References Cited

U.S. PATENT DOCUMENTS 6,166,027 A * 12/2000 Straub et al.

* cited by examiner

Primary Examiner—Ceila Chang
Assistant Examiner—Sonya Wright
(74) Attorney, Agent, or Firm—Norris McLaughlin & Marcus

(57) ABSTRACT

The present invention relates to new substituted pyrazole derivatives, processes for their preparation and their use as medicaments, in particular as medicaments for the treatment of cardiovascular disorders.

10 Claims, No Drawings

SUBSTITUTED PYRAZOLE DERIVATIVES FOR THE TREATMENT OF CARDIOCIRCULATORY DISEASES

Priority is claimed of PCT/EP97/06366, which was filed on Nov. 14, 1997, and of which the present application is a 371.

The present invention relates to new substituted pyrazole derivatives, processes for their preparation and their use as medicaments, in particular as medicaments for the treatment of cardiovascular disorders.

It has already been disclosed that 1-benzyl-3-(substituted heteroaryl)-fused pyrazole derivatives inhibit platelet aggregation (cf. EP 667 345 A1).

The present invention relates to new substituted pyrazole derivatives of the general formula (I)

in which $R^1$ represents a saturated or aromatic 5- or 6-membered heterocycle having up to 3 heteroatoms from the group consisting of S, N and/or O, which can be bonded via a nitrogen atom and which is optionally substituted up to 3 times identically or differently by amino, azido, formyl, mercaptyl, carboxyl, hydroxyl, straight-chain or branched acyl, alkoxy, alkylthio or alkoxycarbonyl each having up to 6 carbon atoms, nitro, cyano, halogen, phenyl or straight-chain or branched alkyl having up to 6 carbon atoms, which for its part can be substituted by hydroxyl, amino, azido, carboxyl, straight-chain or branched acyl, alkoxy, alkoxycarbonyl or acylamino each having up to 5 carbon atoms or by a radical of the formula —$OR^4$, in which $R^4$ denotes straight-chain or branched acyl having up to 5 carbon atoms or a group of the formula —$SiR^5R^6R^7$, in which $R^5$, $R^6$ and $R^7$ are identical or different and denote aryl having 6 to 10 carbon atoms or alkyl having up to 6 carbon atoms, and/or is substituted by a radical of the formula

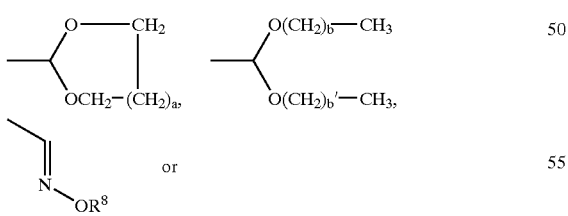

—$S(O)_c$—$NR^9R^{10}$, in which a, b and b' are identical or different and denote a number 0, 1, 2 or 3, $R^8$ denotes hydrogen or straight-chain or branched alkyl having up to 4 carbon atoms, c denotes a number 1 or 2 and $R^9$ and $R^{10}$ are identical or different and denote hydrogen or straight-chain or branched alkyl having up to 10 carbon atoms, which can optionally be substituted by cycloalkyl having 3 to 8 carbon atoms or by aryl having 6 to 10 carbon atoms, which for its part can be substituted by halogen, or denote aryl having 6 to 10 carbon atoms, which is optionally substituted by halogen, or denote cycloalkyl having 3 to 7 carbon atoms, or $R^9$ and $R^{10}$, together with the nitrogen atom, form a 5- to 7-membered saturated heterocycle which can optionally contain a further oxygen atom or a radical —$NR^{11}$, in which $R^{11}$ denotes hydrogen, straight-chain or branched alkyl having up to 4 carbon atoms or a radical of the formula

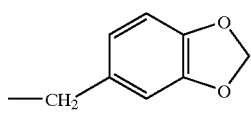

or denotes benzyl or phenyl, where the ring systems are optionally substituted by halogen, $R^2$ and $R^3$, including the double bond, form a 6-membered saturated or aromatic heterocycle having up to 3 heteroatoms from the group consisting of N. S and/or O, which is optionally substituted up to 3 times identically or differently by formyl, carboxyl, hydroxyl, mercaptyl, straight-chain or branched acyl, alkylthio or alkoxycarbonyl each having up to 6 carbon atoms, nitro, cyano, halogen or straight-chain or branched alkyl or alkoxy each having up to 6 carbon atoms, which for its part can be substituted by hydroxyl, amino. carboxyl, straight-chain or branched acyl, alkoxy or alkoxycarbonyl each having up to 5 carbon atoms, and/or the heterocycle is optionally substituted by a group of the formula —$NR^{12}R^{13}$ or —$S(O)_{c'}NR^{9'}R^{10'}$, in which $R^{12}$ and $R^{13}$ are identical or different and denote hydrogen or straight-chain or branched alkyl having up to 6 carbon atoms, or $R^{12}$ denotes hydrogen and $R^{13}$ denotes formyl c', $R^{9'}$ and $R^{10'}$ have the meaning of c, $R^9$ and $R^{10}$ indicated above and are identical to or different from these and/or the heterocycle is optionally substituted by phenyl which for its part can be substituted up to 2 times identically or differently by halogen or by straight-chain or branched alkyl or alkoxy each having up to 6 carbon atoms and/or the heterocycle is optionally substituted by a group of the formula —N=CH—$NR^{14}R^{15}$, in which $R^{14}$ and $R^{15}$ are identical or different and denote hydrogen, phenyl or straight-chain or branched alkyl having up to 6 carbon atoms, A represents a 5- or 6-membered aromatic or saturated heterocycle having up to 3 heteroatoms from the group consisting of S, N and/or O or phenyl, each of which is optionally substituted up to 3 times identically or differently by amino. mercaptyl, hydroxyl, formyl, carboxyl, straight-chain or branched acyl, alkylthio, alkyloxyacyl, alkoxy or alkoxycarbonyl each having up to 6 carbon atoms, nitro, cyano, trifluoromethyl, azido, halogen, phenyl or straight-chain or branched alkyl having up to 6 carbon atoms, which for its part can be substituted by hydroxyl, carboxyl, straight-chain or branched acyl, alkoxy or alkoxycarbonyl each having up to 5 carbon atoms, and/or is substituted by a group of the formula —(CO)$_d$—NR$^{16}$R$^{17}$, in which
d denotes a number 0 or 1,
R$^{16}$ and R$^{17}$ are identical or different and denote hydrogen, phenyl, benzyl or straight-chain or branched alkyl or acyl each having up to 5 carbon atoms, and their isomeric forms and salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can also be separated into the stereoisomerically uniform constituents in a known manner.

Heterocycle in the context of the invention, depending on the abovementioned substituents, in general represents a saturated or aromatic 5- or 6-membered heterocycle which can contain up to 3 heteroatoms from the group consisting of S, N and/or O and which in the case of a nitrogen atom can also be bonded via this. Examples which may be mentioned are: oxadiazolyl, thiadiazolyl, pyrazolyl, pyridyl, pyrimidinyl, pyridazinyl. pyrazinyl, thienyl, furyl, pyrrolyl, tetrahydropyranyl, tetrahydroturanyl, 12,3-triazolyl, thiazolyl, oxazolyl, imidazolyl, morpholinyl or piperidyl. Thiazolyl, furyl, oxazolyl, pyrazolyl triazolyl, pyridyl, pyrimidinyl, pyridazinyl and tetrahydropyranyl are preferred.

Preferred compounds of the general formula (I) according to the invention are those
in which
R$^1$ represents pyrimidinyl, pyridazinyl, pyridyl, pyrazinyl, tetrahydropyranyl, tetrahydrofuranyl, pyrrolyl, furyl, thienyl, imidazolyl, oxazolyl, thiazolyl, 1.2.3-triazolyl, pyrazolyl, oxadiazolyl, thiadiazolyl, isoxazolyl, isothiazolyl, pyranyl or morpholinyl, each of which is optionally substituted up to 3 times identically or differently by amino, formyl, mercaptyl, carboxyl, hydroxyl, straight-chain or branched acyl, alkoxy, alkylthio or alkoxycarbonyl each having up to carbon atoms, nitro, cyano, azido, fluorine, chlorine, bromine, phenyl or straight-chain or branched alkyl having up to 5 carbon atoms, which for its part can be substituted by hydroxyl, amino, azido, carboxyl, straight-chain or branched acyl, alkoxy, alkoxycarbonyl or acylamino each having up to 4 carbon atoms or by a radical of the formula —OR$^4$, in which
R$^4$ denotes straight-chain or branched acyl having up to 4 carbon atoms,
and/or by a radical of the formula

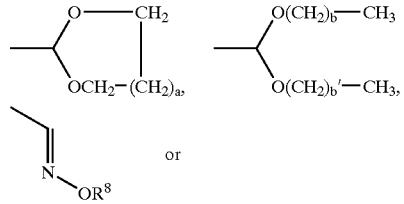

—S(O)$_c$—NR$^9$R$^{10}$,
in which
a, b and b' are identical or different and denote a number 0, 1, 2 or 3.
R$^8$ denotes hydrogen or straight-chain or branched alkyl having up to 3 carbon atoms,
c denotes a number 1 or 2 and
R$^9$ and R$^{10}$ are identical or different and denote hydrogen or straight-chain or branched alkyl having up to 9 carbon atoms, which can optionally be substituted by cyclopropyl, cyclobutyl, cyclopentyl, cyclohexyl, cycloheptyl or naphthyl or phenyl, which for their part can be substituted by fluorine or chlorine, or denote phenyl or naphthyl, each of which is optionally substituted by fluorine or chlorine, or denote cyclopropyl, cyclobutyl, cyclopentyl, cyclohexyl or cycloheptyl, or
R$^9$ and R$^{10}$, together with the nitrogen atom, form a morpholine ring or a radical of the formula

in which R$^{11}$ denotes hydrogen, methyl or a radical of the formula

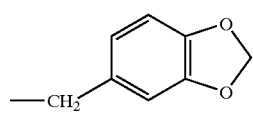

or denotes benzyl or phenyl, where the ring systems are optionally substituted by fluorine or chlorine.
R$^2$ and R$^3$, including the double bond, form a pyridyl, pyrimidinyl, pyrazinyl or pyridazinyl ring, each of which is optionally substituted up to 3 times identically or differently by formyl, carboxyl, hydroxyl, mercaptyl, straight-chain or branched acyl, alkylthio or alkoxycarbonyl each having up to 5 carbon atoms, nitro, cyano, azido, fluorine, chlorine, bromine or straight-chain or branched alkyl or alkoxy each having up to 5 carbon atoms, which for its part can be substituted by hydroxyl, amino, carboxyl, straight-chain or branched acyl, alkoxy or alkoxycarbonyl each having up to 4 carbon atoms.

and/or the abovementioned heterocyclic rings are optionally substituted by a group of the formula —$NR^{12}R^{13}$ or —$S(O)_{c'}NR^{9'}R^{10'}$, in which $R^{12}$ and $R^{13}$ are identical or different and denote hydrogen or straight-chain or branched alkyl having up to 4 carbon atoms, or $R^{12}$ denotes hydrogen and $R^{12}$ denotes formyl c', $R^{9'}$ and $R^{10'}$ have the meaning of c, $R^9$ and $R^{10}$ indicated above and are identical to or different from these and/or the abovementioned heterocyclic rings are optionally substituted by phenyl, which for its part can be substituted by fluorine, chlorine, bromine or by straight-chain or branched alkyl or alkoxy each having up to 4 carbon atoms and/or the abovementioned heterocyclic rings are optionally substituted by a group of the formula

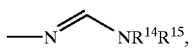

in which $R^{14}$ and $R^{15}$ denote hydrogen or straight-chain or branched alkyl having up to 4 carbon atoms, A represents thienyl, tetrahydropyranyl, tetrahydrofuranyl, phenyl, morpholinyl. pyrimidyl, pyrazinyl, pyridazinyl or pyridyl, each of which is optionally substituted up to 2 times identically or differently by hydroxyl, formyl, carboxyl, straight-chain or branched acyl, alkylthio, alkoxyacyl, alkoxy or alkoxycarbonyl each having up to 4 carbon atoms, fluorine, chlorine, bromine, nitro, cyano, trifluoromethyl or straight-chain or branched alkyl having up to 4 carbon atoms, which for its part can be substituted by hydroxyl, carboxyl, straight-chain or branched acyl, alkoxy or alkoxycarbonyl each having up to 4 carbon atoms, and/or by a group of the formula —$(CO)_d$—$NR^{16}R^{17}$, in which d denotes a number 0 or 1, $R^{16}$ and $R^{17}$ are identical or different and denote hydrogen, phenyl, benzyl or straight-chain or branched alkyl or acyl each having up to 4 carbon atoms, and their isomeric forms and salts.

Particularly preferred compounds of the general formula (I) according to the invention are those
in which $R^1$ represents imidazolyl, furyl, pyridyl, pyrrolyl, pyrazinyl, pyrimidyl, isoxazolyl, oxazolyl or thiazolyl, each of which is optionally substituted up to 3 times identically or differently by formyl, fluorine, chlorine, amino, mercaptyl, cyano, straight-chain or branched acyl, alkylthio, alkoxy or alkoxycarbonyl each having up to 4 carbon atoms or straight-chain or branched alkyl having up to 4 carbon atoms, which for its part can be substituted by hydroxyl, carboxyl, amino, azido, straight-chain or branched acyl, alkoxy, alkoxycarbonyl or acylamino each having up to 3 carbon atoms, and/or by a radical of the formula

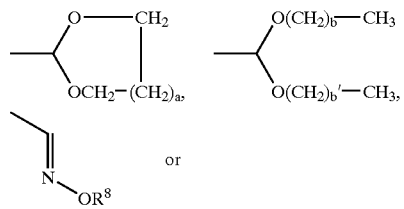

—$S(O)_c$—$NR^9R^{10}$, in which a, b and b' are identical or different and denote a number 0, 1 or 2, $R^8$ denotes hydrogen or methyl, c denotes a number 1 or 2 and $R^9$ and $R^{10}$ are identical or different and denote hydrogen or straight-chain or branched alkyl having up to 9 carbon atoms, which can optionally be substituted by phenyl or naphthyl, or denote phenyl or naphthyl, each of which is optionally substituted by fluorine or chlorine, or denote cyclopropyl or cycloheptyl, or $R^9$ and $R^{10}$, together with the nitrogen atom, form a morpholine ring or a radical of the formula

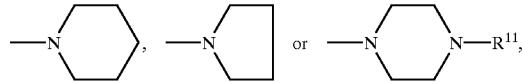

in which $R^{11}$ denotes hydrogen, methyl or a radical of the formula

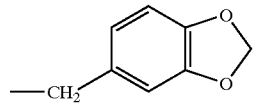

or denotes benzyl or phenyl, where the ring systems are optionally substituted by chlorine, $R^2$ and $R^3$, including the double bond, form a pyridyl, pyrazinyl, pyrimidinyl or pyridazinyl ring, each of which is optionally substituted up to 3 times identically or differently by formyl, mercaptyl, carboxyl, hydroxyl, straight-chain or branched acyl, alkoxy, alkylthio or alkoxycarbonyl each having up to 4 carbon atoms, nitro, cyano, fluorine, chlorine or straight-chain or branched alkyl or alkoxy each having up to 3 carbon atoms, which for its part can be substituted by hydroxyl, amino, carboxyl, straight-chain or branched acyl. alkoxy or alkoxycarbonyl each having up to 3 carbon atoms, and/or the heterocyclic rings are optionally substituted by amino, N,N-dimethyl-amino or by a radical of the formula —NH—CHO or —N═CH—N(CH$_3$)$_2$ and/or by phenyl, which for its part can be substituted by a radical of the formula —O(CH$_3$)$_2$—CH$_3$, A represents tetrahydropyranyl, phenyl, pyrimidyl, thienyl or pyridyl, each of which is optionally substituted up to 2 times identically or differently by formyl, carboxyl, straight-chain or branched acyl, alkylthio, alkyloxyacyl, alkoxy or alkoxycarbonyl each having up to 3 carbon atoms, fluorine, chlorine, bromine, nitro, cyano, trifluoromethyl or straight-chain or branched alkyl having up to 3 carbon atoms, which for its part can be substituted by hydroxyl, carboxyl, straight-chain or branched acyl, alkoxy or alkoxycarbonyl each having up to 3 carbon atoms, and their isomeric forms and salts.

Very particularly preferred compounds of the general formula (I) according to the invention are those in which A represents phenyl, pyrimidyl or fluorine-substituted phenyl or pyrimidyl and their isomeric forms and salts.

Processes for the preparation of the compounds of the general formula (I) according to the invention have additionally been found, characterized in that, depending on the various meanings of the heterocycles mentioned under $R^2$ and $R^3$ above,

[A] compounds of the general formula (II)

$R^1$—D (II)

in which $R^1$ has the meaning indicated above, and

D represents radicals of the formula

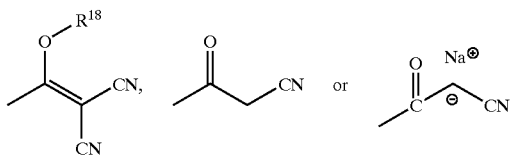

in which $R^{18}$ represents $C_1$–$C_4$-alkyl, are converted by reaction with compounds of the general formula (III)

A—CH$_2$—NH—NH$_2$ (III)

in which

A has the meaning indicated above in inert solvents, if appropriate in the presence of a base, into the compounds of the general formula (IV) or (IVa)

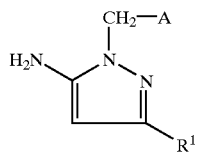 (IV)

and

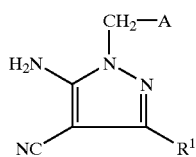 (IVa)

in which

A and $R^1$ have the meaning indicated above, and, in the case of the compounds of the general formula (IVa), then cyclized with carboxylic acids, nitriles, formamides or guanidinium salts, and, in the case of the compounds of the general formula (IV), then cyclized with 1,3-dicarbonyl derivatives, their salts, tautomers, enol ethers or enamines, in the presence of acids and, if appropriate, under microwaves, or

[B] in the case where $R^2$ and $R^3$ together form a pyrazine ring, compounds of the general formula (IV) are first converted by nitrosation into the compounds of the general formula (V)

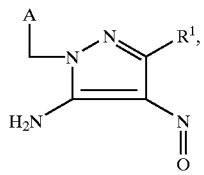 (V)

in which

A and $R^1$ have the meaning indicated above, in a second step, by means of a reduction, the compounds of the general formula (VI)

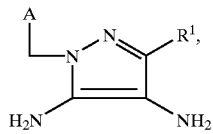 (VI)

in which

A and $R^1$ have the meaning indicated above, are prepared and finally cyclized with 1,2-dicarbonyl compounds, preferably aqueous glyoxal solution, or

[C] compounds of the general formula (VII)

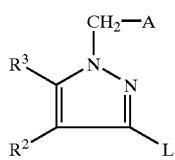 (VII)

in which

A¹, R² and R³ have the meaning indicated above,
and

L represents a radical of the formula —SnR¹⁹R²⁰R²¹, ZnR²², iodine, bromine or triflate, in which
R¹⁹, R²⁰ and R²¹ are identical or different and denote straight-chain or branched alkyl having up to 4 carbon atoms,
and
R²² denotes halogen,
are reacted with compounds of the general formula (VIII)

R¹—T  (VIII)

in which
R¹ has the meaning indicated above
and
if L=SnR¹⁹R²⁰R²¹ or ZnR²²,
T represents triflate or halogen, preferably bromine,
and
if L=iodine, bromine or triflate,
T represents a radical of the formula SnR¹⁹'R²⁰'R²¹', ZnR²²' or BR²³'R²⁴',
in which
R¹⁹', R²⁰', R²¹' and R²²' have the meaning of R¹⁹, R²⁰, R²¹ and R²² indicated above and are identical to or different from these,
R²³' and R²⁴' are identical or different and denote hydroxyl, aryloxy having 6 to 10 carbon atoms or straight-chain or branched alkyl or alkoxy each having up to 5 carbon atoms, or together form a 5- or 6-membered carbocyclic ring, in a palladium-catalysed reaction in inert solvents, if appropriate in the presence of a base,

[D]

if R¹ = 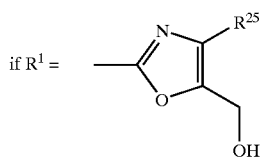

in which
R²⁵ denotes (C₁–C₆)-alkyl which is optionally substituted by halogen,
compounds of the general formula (IX)

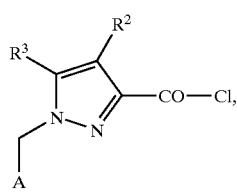
(IX)

in which
A, R² and R³ have the meaning indicated above,
are converted either directly by reaction with the compound of the formula (X)

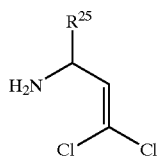
(X)

in which
R²⁵ has the meaning indicated above,
in the system NaOCO—CH₃/N-methylpyrrolidine into the compounds of the general formula (Ia)

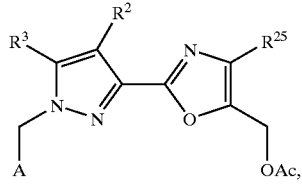
(Ia)

in which
R², R³ and A and R²⁵ have the meaning indicated above,
and then, by action of potassium hydroxide in methanol, the acetyl group is removed,
or
first by reaction of the compounds of the general formula (IX) with the compound of the formula (X) the compounds of the general formula (XI)

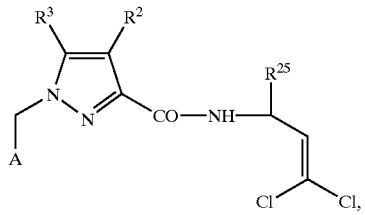
(XI)

in which
R², R³, A and R²⁵ have the meaning indicated above,
are prepared,
and in a further step by action of potassium hydroxide the hydroxymethyl compounds are prepared,
and in the case of the groups —S(O)Z_cNR⁹R¹⁰ and —S(O)_cNR⁹R¹⁰, starting from the unsubstituted compounds of the general formula (I), first reacted with thionyl chloride and in a second step with the appropriate amines
and, if appropriate, the substituents mentioned under R¹, R², R³ and/or A are varied or introduced according to customary methods, preferably by chlorination, catalytic hydrogenation, reduction, oxidation, removal of protective groups and/or nucleophilic substitution.

The heterocycles mentioned under R² and R³ can also be introduced by reaction of the appropriately substituted compounds of the general formula (II) according to other known heterocyclic syntheses.

The process according to the invention can be illustrated by way of example by the following reaction scheme:

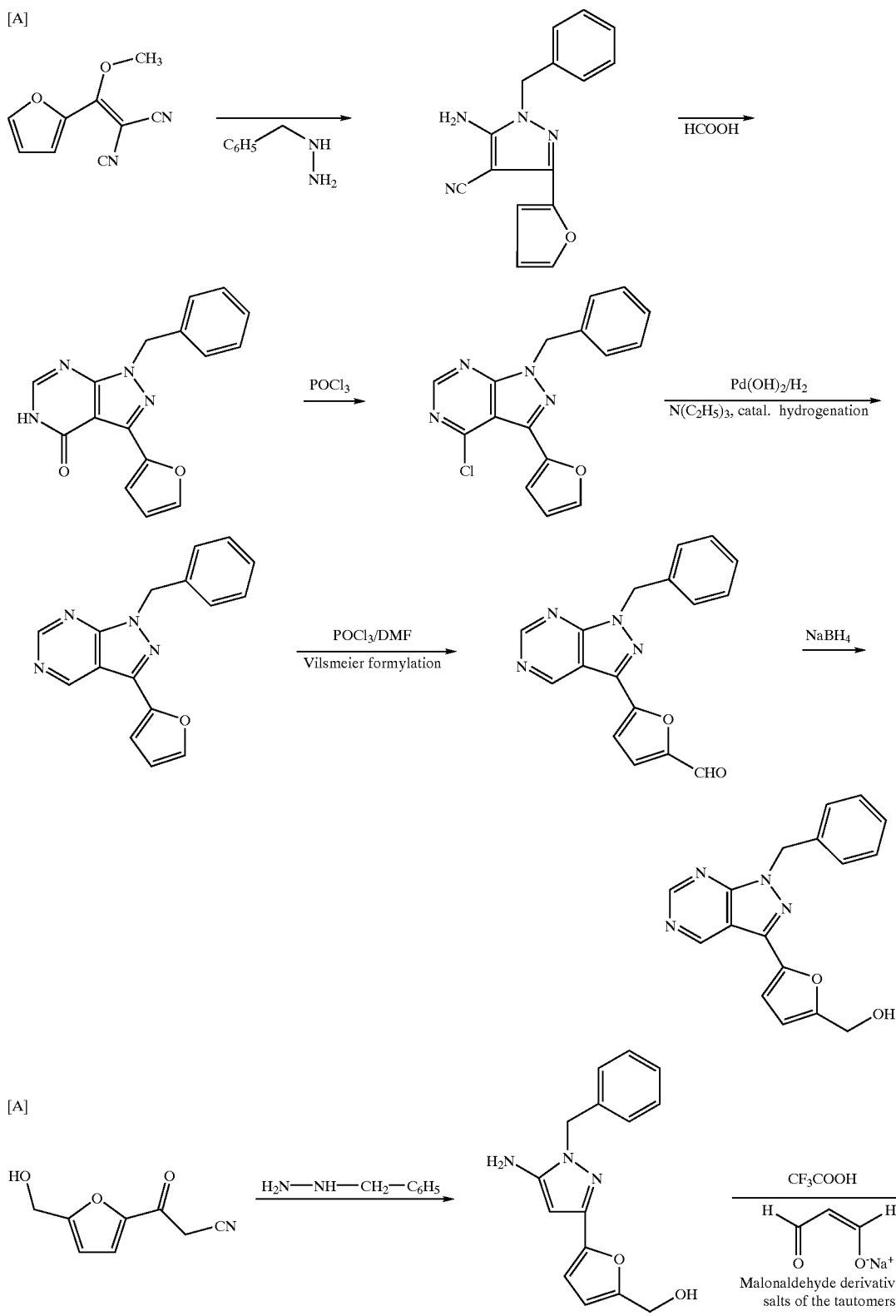

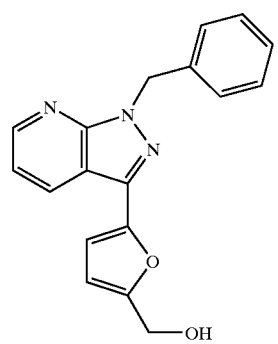
[A] and derivatives
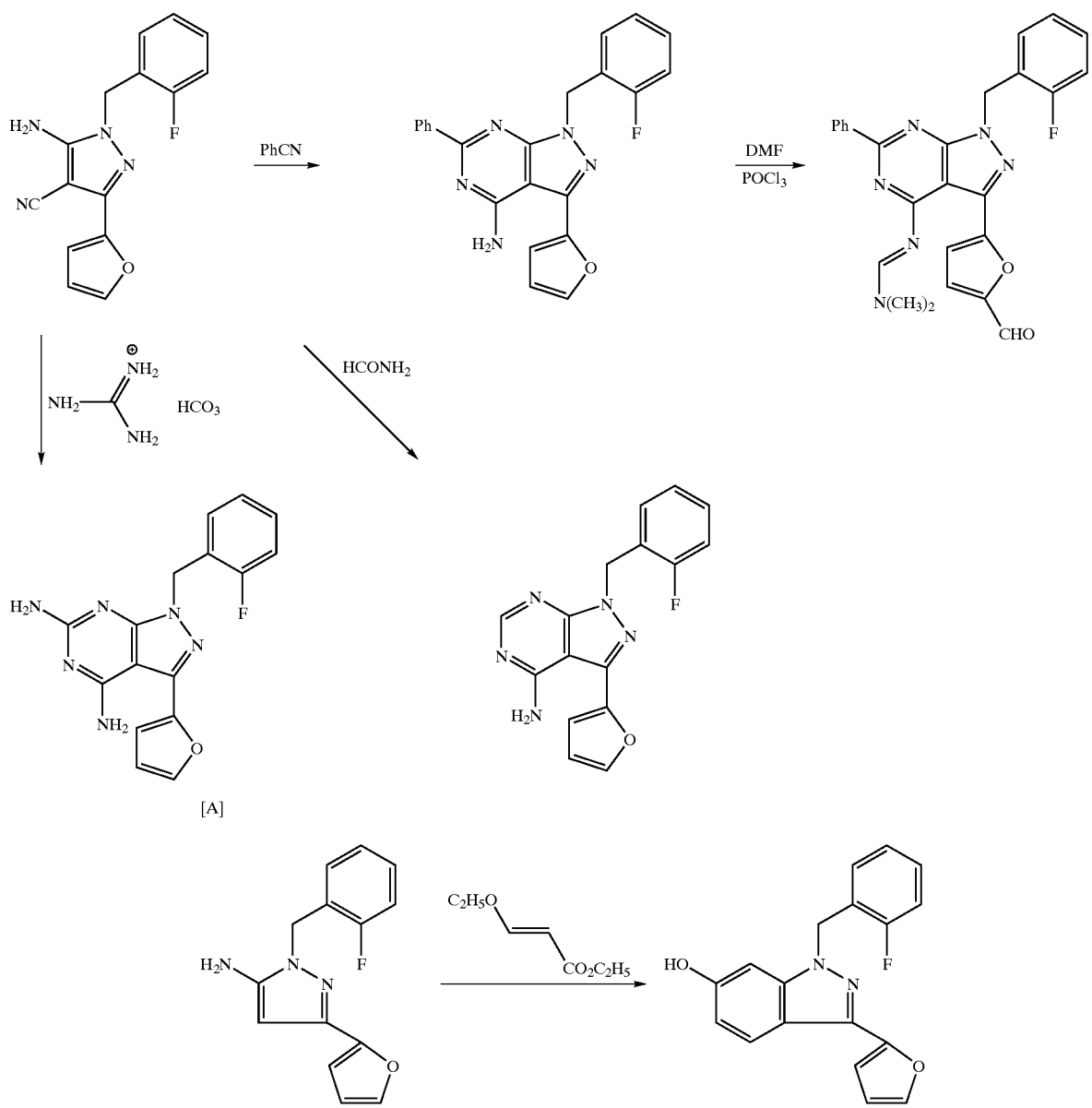
[A]

[A]
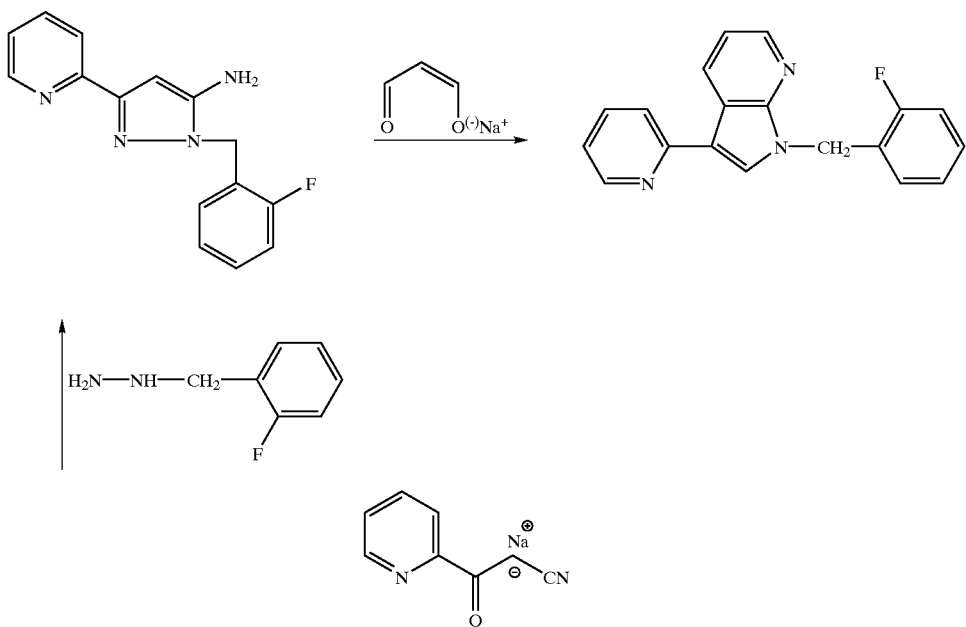
[B]
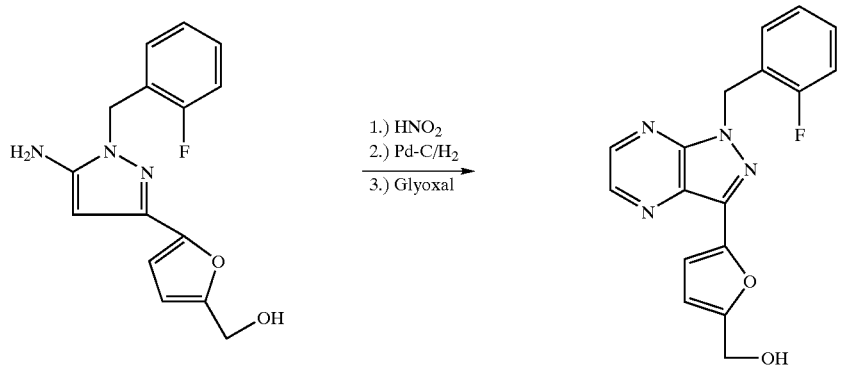
[C]
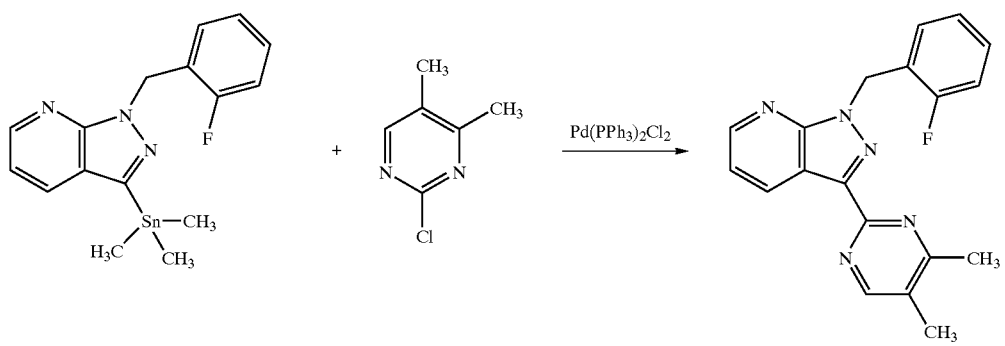

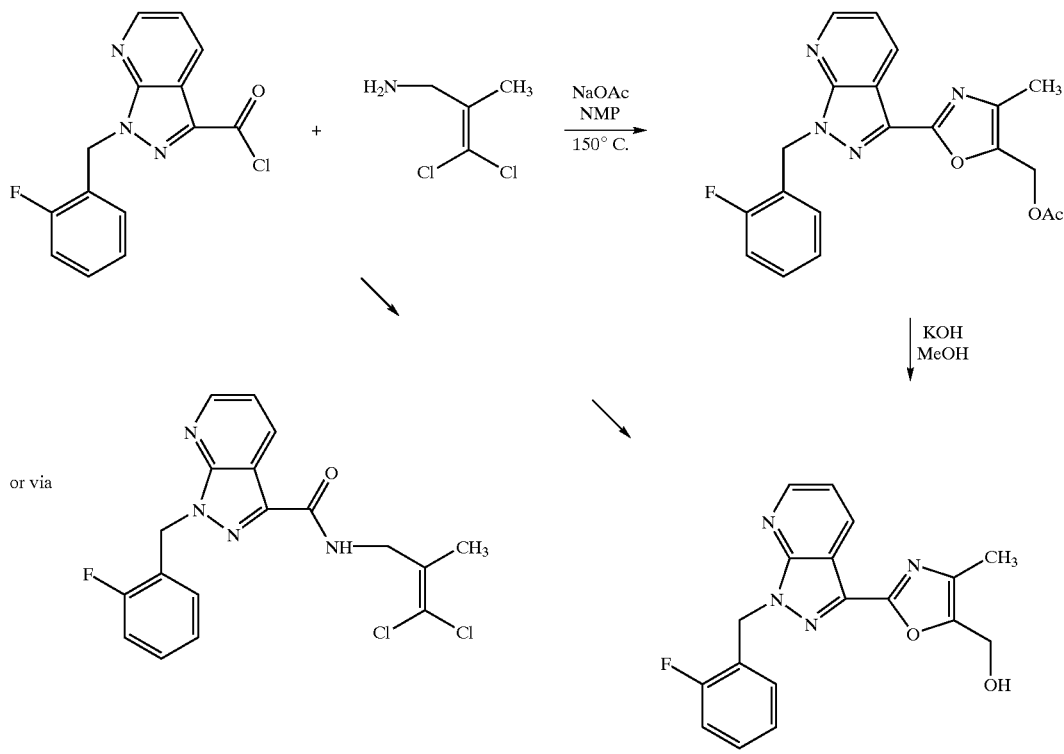

Suitable solvents here for the individual steps of the processes are inert organic solvents which do not change under the reaction conditions. These include ethers, such as diethyl ether or tetrahydrofuran, DME, dioxane, alcohols such as methanol and ethanol, halogenohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Tetrahydrofuran, dimethylformamide, toluene, dioxane or dimethoxyethane are particularly preferred.

Bases employed for the processes according to the invention can in general be inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)-amines) such as triethylamine, or heterocycles such as 1,4-diazabicyclo[2,2,2]octane (DABCO), 1,8-diazabicyco[5,4,0]undec-7-ene (DBU). pyridine, diaminopyridine, methylpiperidine or morpholine. It is also possible to employ as bases alkali metals such as sodium and their hydrides such as sodium hydride. Sodium and potassium carbonate, triethylamine and sodium hydride are preferred.

The base is employed in an amount from 1 mol to 5 mol, preferably from 1 mol to 3 mol, relative to 1 mol of the compound of the general formula (II).

The reaction is in general carried out in a temperature range from 0° C. to 150° C. preferably from +20° C. to +110° C.

The reaction can be carried out at normal, elevated or at reduced pressure (e.g. 0.5 to 5 bar). In general, it is carried out at normal pressure.

Suitable acids for the cyclization are in general protonic acids. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals such as, for example, methanesulphonic acid, ethanesulphonic acid, benzenesulphonic acid or toluenesulphonic acid.

The catalytic hydrogenation can in general be carried out by means of hydrogen in water or in inert organic solvents such as alcohols, ethers or halogenohydrocarbons, or mixtures thereof with catalysts such as Raney nickel, palladium, palladium on animal charcoal or platinum, or with hydrides or boranes in inert solvents, if appropriate in the presence of a catalyst.

Chlorination is in general carried out using the customary chlorinating agents such as, for example, $PCl_3$, $PCl_5$, $POCl_3$ or elemental chlorine. $POCl_3$ is preferred in the context of the invention.

If the radicals of the formulae —$S(O)_c NR^9 R^{10}$ and —$S(O)_c NR^{9'} R^{10'}$ are present, the corresponding unsubstituted compounds are first reacted with thionyl chloride. In a further step, the reaction with the amines is carried out in one of the abovementioned ethers, preferably dioxane. If c=2, an oxidation is then carried out according to customary methods. The reactions are carried out in a temperature range from 0° C. to 70° C. and normal pressure.

The nucleophilic substitutions and Vilsmeier reactions are carried out according to customary, published methods.

The reductions are in general carried out using reducing agents, preferably using those which are suitable for the reduction of carbonyl to hydroxyl compounds. Reduction using metal hydrides or complex metal hydrides in inert solvents is particularly suitable here, if appropriate in the presence of a trialkylborane. Preferably, the reduction is carried out using complex metal hydrides such as, for example, lithium borohydride, sodium borohydride, potassium borohydride, zinc borohydride, lithium trialkylborohydride, diusobutylaluminium hydride or lithium aluminium hydride. Reduction with dilsobutylaluminium hydride and sodium borohydride is very particularly preferred.

The reducing agent is in general employed in an amount from 1 mol to 6 mol, preferably from 1 mol to 4 mol relative to 1 mol of the compounds to be reduced.

The reduction in general proceeds in a temperature range from −78° C. to +50° C., preferably from −78° C. to 0° C. in the case of DIBAH, 0° C. to room temperature in the case of $NaBH_4$.

The reduction in general proceeds at normal pressure, but it is also possible to work at elevated or reduced pressure.

The compounds of the general formulae (II) and (III) are known per se or can be prepared by customary methods [cf, for this: J. Hromatha et al., Monatsh. Chem. 1976, 107, 233)

The compounds of the general formulae (IV), (IVa), (V) and (VI) are known in some cases and can be prepared as described above.

Suitable solvents here for process [C] are inert organic solvents which do not chance under the reaction conditions. These include ethers, such as diethyl ether or tetrahydrofuran, DME, dioxane, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Tetrahydrofuran, dimethylformamide, toluene, dioxane or dimethoxyethane is particularly preferred.

The reaction is in general carried out in a temperature range from 0° C. to 150° C. preferably from +20° C. to +110° C.

The reaction can be carried out at normal, elevated or at reduced pressure (e.g. 0.5 to 5 bar). In general, it is carried out at normal pressure.

Suitable palladium compounds in the context of the present invention are in general $PdCl_2(P(C_6H_5)_3)_2$, palladium bis-dibenzylideneacetone $(Pd(dba)_2)$, [1,1'-bis-(diphenylphosphino)ferrocene]-palladium(II) chloride (Pd $(dppf)Cl_2$) or $Pd(P(C_6H_5)_3)_4$, $Pd(P(C_6H_5)_3)_4$ is preferred.

The compounds of the general formula (VIII) are known per se or can be prepared by customary methods.

The compounds of the general formula (VII) are known in some cases or, in the case of the stannyls, are new and can then be prepared, for example, by reacting the compounds of the general formula (XII)

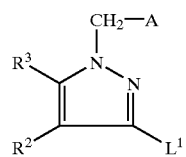

(XII)

in which
R², R³ and A have the meaning indicated above,
L¹ represents triflate or halogen, preferably iodine,
with compounds of the general formula (XIII)

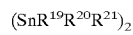

(XIII)

in which
$R^{19}$, $R^{20}$, $R^{21}$ have the meaning indicated above
as described above with palladium catalysis.

The compounds of the general formulae (XII) and (XIII) are known per se or can be prepared by customary methods.

Process [D] according to the invention is carried out using one of the abovementioned bases, preferably in N-methylpyrrolidone, in a temperature range from 100° C. to 200° C. preferably at 150° C.

The compounds of the general formulae (IX) and (X) are known or can be prepared by customary methods.

The compounds of the general formula (la) and (XI) are new and can be prepared as described above.

In the case in which typical protective groups are employed in the course of derivatization reactions, their removal is in general carried out in one of the abovementioned alcohols and/or THF or acetone, preferably methanol/THF in the presence of hydrochloric acid or trifluoroacetic acid or toluenesulphonic acid in a temperature range from 0° C. to 70° C., preferably at room temperature and normal pressure.

The compounds of the general formula (I) according to the invention show an unforeseeable, valuable spectrum of pharmacological action.

The compounds of the general formula (I) lead to a vasorelaxation/inhibition of platelet aggregation and to a blood pressure fall and also to an increase in the coronary blood flow. These actions are mediated via a direct stimulation of soluble guanylate cyclase and an intracellular cGMP increase. Additionally, the compounds according to the invention increase the action of substances which raise the cGMP level, such as, for example. EDRF (endothelium-derived relaxing factor), NO donors, protoporphvrin IX, arachidonic acid or phenylhydrazine derivatives.

They can therefore be employed in medicaments for the treatment of cardiovascular disorders such as, for example, for the treatment of high blood pressure and cardiac insufficiency, stable and unstable angina pectoris, peripheral and cardiac vascular disorders, arrhythmias, for the treatment of thromboembolic disorders and ischaemias such as myocardial infarct, stroke, transitory and ischaemic attacks, peripheral circulatory disorders, prevention of restenoses such as after thrombolysis therapy, percutaneous transluminal angioplasty (PTA), percutaneous transluminal coronary angioplasty (PTCA), bypass and also for the treatment of arteriosclerosis and disorders of the urogenital system such as, for example, prostate hypertrophy, erectile dysfunction and incontinence.

The invention moreover includes the combination of the compounds of the general formula (I) according to the invention with organic nitrates and NO donors.

Organic nitrates and NO donors in the context of the invention are in general substances which display their therapeutic action via the release of NO or NO species. Sodium nitroprusside, nitroglycerine, isosorbide dinitrate, isosorbide mononitrate, molsidomine and SIN-1 are preferred.

The invention additionally includes combination with compounds which inhibit the degradation of cyclic guanosine monophosphate (cGMP). These are, in particular. inhibitors of phosphodiesterases 1, 2 and 5; nomenclature according to Beavo and Reifsnyder (1990) TiPS 11 p. 150 to 155. The action of the compounds according to the invention is potentiated and the desired pharmacological effect is increased by these inhibitors.

To determine the cardiovascular actions, the following investigations were carried out: in in vitro investigations on cells of vascular origin, the influx on guanylate cyclase-dependent cGMP formation was tested with and without NO donor. The anti-aggregatory properties were shown on human platelets stimulated with collagen. The vasorelaxant action was determined in rabbit aortal rings precontracted with phenylephrine. The hypotentive action was investigated in anaesthetized rats.

Stimulation of Soluble Guanylate Cyclase in Primary Endothelial Cells

Primary endothelial cells were isolated from rabbit aortas by treatment with collagenase soln. The cells were then cultured in culture medium at 37° C./5% $CO_2$ until confluence was reached. For the investigations, the cells were passaged, inoculated into 24-hole cell culture plates and subcultured until reaching confluence ($\sim 2 \times 10^5$ cells/hollow). For the stimulation of endothelial guanylate cyclase, the culture medium was aspirated and the cells were washed once with Ringer solution. After removing the Ringer solution, the cells were incubated for 10 minutes at 37° C./5% $CO_2$ in stimulation buffer with or without NO donor (sodium nitroprusside, SNP, 1 $\mu$M). Following this, the test substances (final concentration 1 $\mu$M) were added to the cells by pipette and they were incubated for a further 10 minutes. After the end of the incubation time, the buffer solution was aspirated and cold stop buffer at 4° C. was added to the cells. The cells were then lysed at −20° C. for 16 hours. The supernatants containing the intracellular cGMP were then removed and the cGMP concentration was determined by means of the cGMP-SPA system (Amersham Buchler, Brunswick).

TABLE A

| Ex. No. | cGMP increase (%) |
| --- | --- |
| 14 | >1000 |
| 15 | 504 |
| 16 | 652 |
| 17 | >1000 |
| 32 | 135 |

Vasorelaxant Action In Vitro

Rabbits are anaesthetized by a blow to the neck and exsanguinated. The aorta is removed, freed from adhering tissue, divided into 1.5 mm wide rings and individually transferred under a pretension into 5 ml organ baths containing warm, carbogen aerated Krebs-Henseleit solution at 37° C. of the following composition (mM): NaCl: 119; KCl: 4.8: $CaCl_2 \times 2$ $H_2O$: 1; $MgSO_4 \times 7$ $H_2O$: 1.4; $KH_2PO_4$: 1.2; $NaHCO_3$: 25; glucose: 10.

The contractility is detected using Statham UC2 cells, amplified and digitalized by means of A/D converters (DAS-1802 HC, Keithley Instruments Munich), and recorded in parallel on linear recorders. To produce a contraction, phenylephrine is added to the bath cumulatively in increasing concentration.

After several control cycles, the substance to be investigated is investigated in each further passage in increasing dosage in each case and the height of the contraction is compared with the height of the contraction achieved in the last preliminary passage. from this, the concentration is calculated which is necessary in order to reduce the height of the control value by 50% ($IC_{50}$). The standard administration volume is 5 $\mu$l and the proportion of DMSO in the bath solution corresponds to 0.1%.

TABLE B

| Ex. No. | Aorta ($IC_{50}$) $\mu$M |
| --- | --- |
| 14 | 1.8 |
| 15 | 13.0 |
| 16 | 1.7 |

Blood Pressure Measurements in Anaesthetized Rats

Male Wistar rats having a body weight of 300–350 g are anaesthetized with thiopental (100 mg/kg i.p.) After tracheotomy, a catheter is inserted in the femoral artery for blood pressure measurement. The substances to be tested are administered orally in various doses by means of stomach tube as a suspension in Tylose solution.

TABLE C

| Ex. No. | Dose (mg/kg) | Max blood pressure fall (mm Hg) | Time (min) |
| --- | --- | --- | --- |
| 13 | 10 | −13 | 60 |
|    | 30 | −23 | 60 |
| 14 | 10 | −18 | 40 |
|    | 30 | −21 | 50 |
| 16 | 10 | −9 | 50 |
|    | 30 | −16 | 50 |

Inhibition of Platelet Aggregation In Vitro

For determination of the platelet aggregation-inhibiting action, blood from healthy subjects of both sexes was used. As an anticoagulant, 9 parts of blood were admixed to one part of 3.8% strength aqueous sodium citrate solution. By means of centrifugation, platelet-rich citrate plasma (PRP) was obtained from this blood (Jurgens/Beller, Klinische Methoden der Blutgerinnungsanalyse [Clinical Methods of Blood Coagulation Analysis]; Thieme Verlag, Stuttgart, 1959).

For these investigations, 445 $\mu$l of PRP and 5 $\mu$l of the active compound solution were preincubated at 37° C. in a water bath. The platelet aggregation was then determined at 37° C. in an aggregometer by the turbidometric method (Born, G. V. R., J. Physiol. (London), 168, 178–195, 1963). For this purpose, the preincubated sample was treated with 50 $\mu$l of collagen, an aggregation-inducing agent, and the change in the optical density was determined. For quantitative evaluation, the maximum aggregation response was determined and from this the percentage inhibition compared to the control was calculated.

The compounds described in the present invention are also active compounds for the control of illnesses in the central nervous system which are characterized by disorders of the NO/cGMP system. In particular, they are suitable for the elimination of cognitive deficits, for the improvement of learning and memory power and for the treatment of Alzheimer's disease. They are also suitable for the treatment of disorders of the central nervous system such as anxiety, tension and depressive states, central nervous system-related sexual dysfunctions and sleep disorders, and also for the regulation of pathological disorders of foodstuff, tea, coffee, alcohl, tobacco and addictive drug intake.

Furthermore, these active compounds are also suitable for the regulation of the cerebral blood circulation and are thus effective agents for the control of migrane.

They are also suitable for the prophylaxis and control of the sequelae of cerebral infarcts (cerebral apoplexy) such as stroke, cerebral ischaemias and craniocerebral trauma. The compounds according to the invention can also be employed for the control of states of pain.

The present invention includes pharmaceutical preparations which, in addition to non-toxic, inert pharmaceutically acceptable excipients, contain one or more compounds according to the invention or which consist of one or more active compounds according to the invention, as well as processes for the production of these preparations.

The active compound(s) can optionally be present in one or more of the excipients indicated above and also in microencapsulated form.

The therapeutically active compounds should be present in the abovementioned pharmaceutical preparations in a concentration from approximately 0.1 to 99.5, preferably from approximately 0.5 to 95, % by weight of the total mixture.

In addition to the compounds according to the invention, the abovementioned pharmaceutical preparations can also contain further pharmaceutical active compounds.

In general, it has proved advantageous both in human and in veterinary medicine to administer the active compound(s) in total amounts from approximately 0.5 to approximately 500, preferably 5 to 100, mg/kg of body weight every 24 hours, if appropriate in the form of several individual doses, to achieve the desired results. An individual dose contains the active compound(s) preferably in amounts from approximately 1 to approximately 80, in particular 3 to 30, mg/kg of body weight.

Abbreviations

MeOH=methanol

E=ethanol

EA=ethyl acetate

T=toluene

Ph=phenyl

The numbers after the solvent abbreviations in the following tables under the column $R_f$ denote parts by weight.

Starting Compounds

EXAMPLE I A

5-Amino-1-benzyl-3-(5-hydroxymethyl-2-furyl)-pyrazole

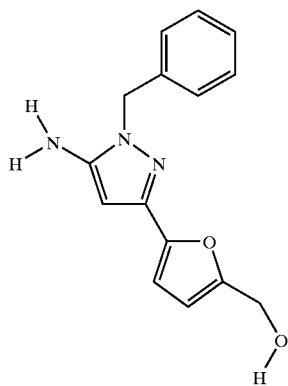

44.1 g (817 mmol) of sodium methoxide is added with stirring to a solution of 79.5 g (408 mmol) of benzylhydrazine dihydrochloride in 1.3 l of ethanol. After 15 min 67.4 g (408 mmol) of 2-cyanomethylcarbonyl-5-hydroxymethylfuran are added and the mixture is stirred under reflux for 3 hours. After cooling, 1 l of water is added, the ethanol part is evaporated in vacuo and the precipitated crystals are filtered off with suction. After washing, with water and then with ether, the precipitate is dried over $P_2O_5$, 91 g(83% of theory) of product having an m.p. of 163° C. are obtained.

The compounds shown in Table 1A were prepared analogously:

TABLE 1A

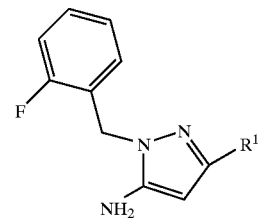

| Ex. No. | $R^1$ | m.p. [° C.] | $R_f$ | Yield [% of theory] |
|---|---|---|---|---|
| 2A | 2-furyl | 124 | 0.63 (T1E1) | 49 |
| 3A | 2-pyrimidinyl | 178 | 0.49 (MeOH1E4) | 66.5 |
| 4A | 2-pyridyl | 130 | 0.08 (T1E1) | 30 |

EXAMPLE 5A

5-Amino-1-(2-fluorobenzyl)-3-(5-hydroxymethyl-2-furyl)-4-nitroso-pyrazole

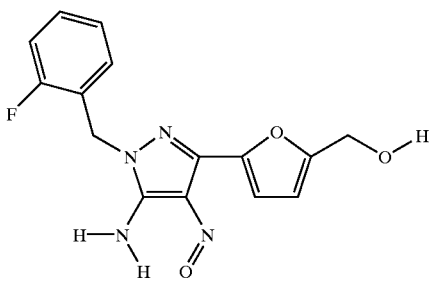

10 g (34.8 mmol) of 5-amino-1-(2-fluorobenzyl)-3-(5-hydroxymethyl-2-furyl)-pyrazole are initially introduced in a mixture of 66 ml of ethanol and 26.7 ml of 5% strength aqueous hydrochloric acid, treated in the course of 5 minutes with 26.4 ml of a 15% strength ethanolic solution of ethyl nitrite and stirred at room temperature for 1 h. The deep violet reaction solution is added to aqueous potassium carbonate solution and extracted with ethyl acetate. After evaporating the organic phase in vacuo, 8 g of the residue are obtained, which can be immediately reacted further. ($R_f$=0.17, T1E1, $SiO_2$).

EXAMPLE 6A 4,5-Diamino-1-(2-fluorobenzyl)-3-(5-hydroxymethyl-2-furyl)-pyrazole

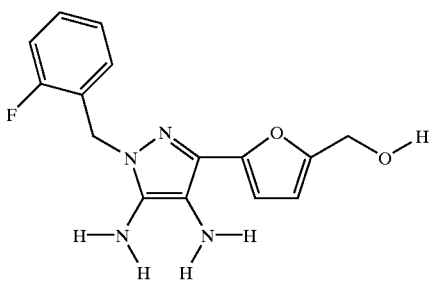

The compound from Example 5A (8 g) is dissolved in ethanol, treated with 0.5 g of 5% strength palladium on carbon and hydrogenated for 15 minutes in a Parr apparatus at a hydrogen pressure of 2 bar. The solution is filtered off with suction through kieselguhr and used for the next batch ($R_f$=0.21, T1E1, $SiO_2$).

EXAMPLE 7A

3-Amino-2-(2-fluorobenzyl)-pyrazole

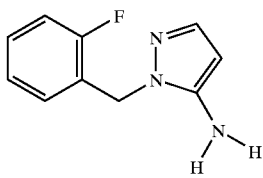

Was obtained analogously to the process described in the patent Fr. 1403372 (Chem. Abstr. 1965, 63, 14871a).

EXAMPLE 8A 1-(2-Fluorobenzyl)-pyrazolo[3,4-b]pyrimidine

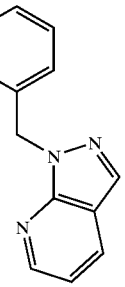

32 g of 3-amino-2-(2-fluorobenzyl)-pyrazole are dissolved in 1.5 l of dioxane and treated with 31.45 g of dimethylaminoacrolein. The mixture is warmed to 50° C. and 16.65 g of trifluoroacetic acid are then added. The mixture is boiled for 60 hours, the solvent is then evaporated in vacuo, the residue is treated with water and the mixture is extracted with ethyl acetate. The organic phase is dried using $Na_2SO_4$ and evaporated in vacuo, and the residue is chromatographed on silica gel. After elution with toluene →toluene/ethyl acetate 9:1, 17.3 g (46.3% of theory) of the title compound having an $R_f$ of 0.69 ($SiO_2$, $T_1E_1$) are obtained.

EXAMPLE 9A

3-Bromo-1-(2-fluorobenzyl)-pyrazolo[3,4-b]pyrimidine

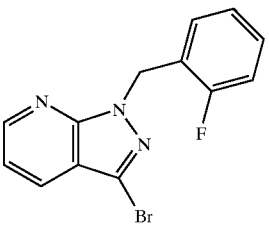

8 g (35.2 mmol) of 1-(2-fluorobenzyl)pyrazolo[3,4-b]pyrimidine are dissolved in 284 ml of chloroform and treated slowly at room temperature with 14 g (87.3 mmol) of bromine. The mixture is stirred overnight and a further 1.2 ml of bromine are then added dropwise. After 2 h, the reaction is terminated and evaporated in vacuo. The residue is treated with 20 ml of ethyl acetate and induced to crystallize. After washing the crystals with ether, 7.5 g (70% of theory) of the title compound having an $R_f$ of 0.2 ($SiO_2$, toluene) are obtained.

EXAMPLE 10A 1-(2-Fluorobenzyl)-3-trimethylstannylpyrazolo[3,4-b]pyrimidine

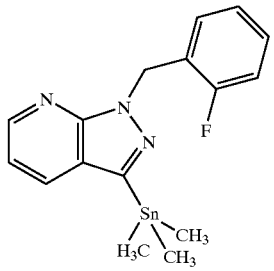

1.22 g (4 mmol) of 3-bromo-1-(2-fluorobenzyl)pyrazolo[3.4-b]pyrimidine are dissolved in 200 ml of dioxane under argon and treated with 4.5 g (13.74 mmol) of hexamethyldistannane and 1.2 g of tetrakis(triphenylphosphine)palladium. The mixture is stirred overnight at 100° C., added to water and extracted with ethyl acetate. The organic phase is dried using $Na_2SO_4$, evaporated in vacuo and chromatographed on silica gel. After elution with toluene, 1.4 g (89.7% of theory) of the title compound having an $R_f$ of 0.074 ($SiO_2$, toluene) are obtained.

EXAMPLE 11A

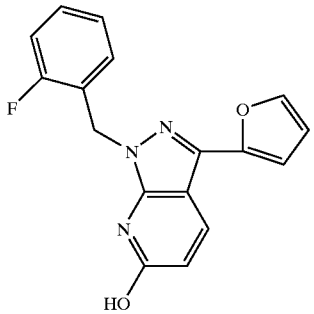

500 mg of 1-(2-fluorobenzyl)pyrazolo[3,4-b]pyridine-3-carboxylic acid (1.84 mmol) are partly dissolved in 10 ml of methylene chloride. 400 mg of N-(3-dimethylaminopropyl)-N'-ethylcarbodiimide hydrochloride (2.3 mmol) are added. The mixture is stirred at RT for 10 min (complete solution), then a solution of 260 mg of 1,1-dichloro-3-amino-but-1-ene (1.84 mmol) in 5 ml of methylene chloride is added dropwise.

After approximately 3 h, the mixture is concentrated and purified on silica gel (solvent: cyclohexane/EA 1:1). 340 mg (47%) of 1-(2-fluorobenzyl)-3-( 1,1-dichlorobut-1-en-3-yl-amido)pyrazolo[3,4]pyridine are obtained, $R_f$ 0.35 (cyclohexane:EA 2:1). MS (ESI-POSITIVE): 417 (27, [M+Na]⁻); 415 (42, [M+Na]⁻); 395 (60, [M+H]⁻); 393 (100, [M+H]⁻).

PREPARATION EXAMPLES

Example 1

1-(2-Fluorobenzyl)-3-(2-hydroxymethyl-2-furyl)pyrazolo[3,4-b]pyrazine

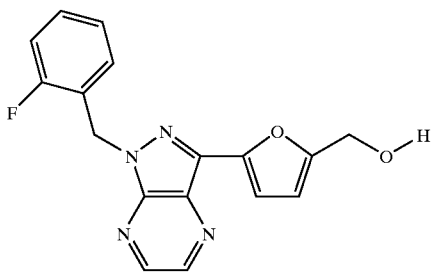

The crude batch (8 g in 200 ml of ethanol) from Example 6A is treated with 4.61 g of a 40% strength aqueous glyoxal solution and stirred at room temperature for 10 h. The mixture is evaporated in vacuo and chromatographed on $SiO_2$ using toluene/ethyl acetate mixtures. After crystallization with ether, 0.57 g (7.6% of theory) of the title compound having an m.p. of 194° C. is obtained.

Example 2

1-(2-Fluorobenzyl)-3-(2-furyl)-6-hydroxypyrazolo[3,4-b]pyridine 7 g (27.2 mmol) of 5-amino-1-(2-fluorobenzyl)-3-(2-furyl)pyrazole, 3.94 g (27.3 mmol) of ethyl 3-ethoxyacrylate and 1.96 ml (27.3 mmol) of trifluoroacetic acid are intimately mixed and made to react for 2 minutes in a microwave oven. The mixture is added to a solution of 10 g of $K_2HPO_4$ in 500 ml of water and extracted with 500 ml of ethyl acetate. After drying of the organic phase with $MgSO_4$, 30 g of silica gel are added and the mixture is evaporated in vacuo. The residue is chromatographed on a silica gel column using a toluene-ethyl acetate gradient. The first fraction is crystallized using ether and affords 1.8 g (21.4% of theory) of the title compound having an m.p. of 250° C.

The compounds listed in Table 1 were prepared in analogy to the procedure of Example 2:

TABLE 1

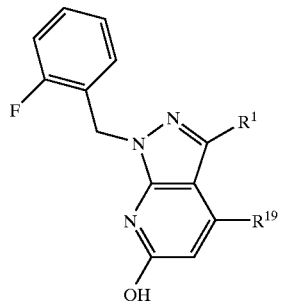

| Ex. No. | R¹ | R¹⁹ | Yield (% of theory) | $R_f$/m.p. °C. |
|---|---|---|---|---|
| 3* | 2-furyl | —CH₃ | 24 | 226 |
| 4 | 2-pyridyl | H | | 0.8 (EA) |

*from ethyl acetoacetate

Example 5

4-Amino-1-(2-fluorobenzyl)-3-(2-furyl)pyrazolo[3,4-d]pyrimidine

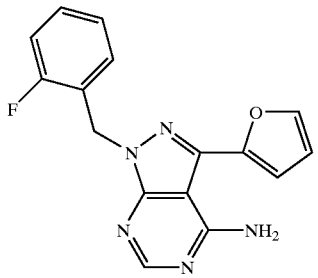

2 g (7.1 mmol) of 5-amino-4-cyano-1-(2-fluorobenzyl)-3-(2-furyl)pyrazole and 30 ml of formamide are stirred first at 100° C. and then at 195° C. for 3 h. The material crystallizing on cooling is filtered off with suction and washed with cold formamide, the residue is taken up in ethyl acetate and the solution is washed with water. After drying and evaporating the organic phase, 2.13 g (97% of theory) of the title compound having an m.p. of 190° C. are obtained. $R_f$=0.07 (T1E1).

The compounds listed in Table 2 are obtained in an analogous manner, for example. from 2-propyloxyphenylnitrile, benzonitrile or guanidinium hydrogencarbonate:

TABLE 2

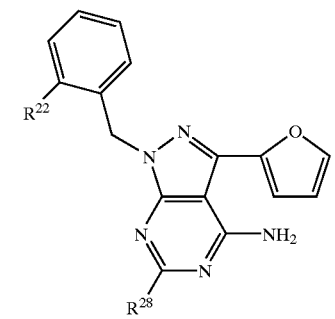

| Ex. No. | R²⁷ | R²⁸ | m.p. [° C.] | $R_f$ | Yield [% of thery] |
|---|---|---|---|---|---|
| 6 | F | 2-propyloxyphenyl | 187 | 0.6 (T1E1) | 42.7 |
| 7 | F | Ph | 205 | 0.69 (T1E1) | 100 |
| 8 | F | NH₂ | 205 | 0.22 (EA) | 71 |
| 9 | H | H | 174 | 0.15 (T1E1) | 90 |

Example 10

1-Benzyl-3-(2-furyl)-4-hydroxypyrazolo[3,4-d]pyrimidine

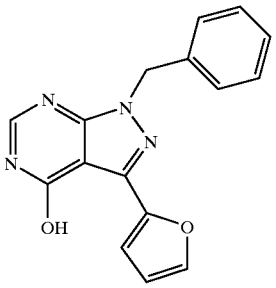

6.14 g (23.2 mmol) of 5-amino-1-benzyl-4-cyano-3-(2-furyl)pyrazole ($R_f$=0.6) are boiled for 3.75 h in 100 ml of formic acid. The batch is then evaporated in vacuo. The residue is treated with water and the mixture is extracted by shaking with ethyl acetate. The insoluble portion is filtered off with suction and affords 5.1 g of the target compound (m.p.=242° C., $R_f$=0.3, SiO₂, toluene/ethyl acetate =1:1). By evaporating the organic phase, further quantities can be isolated.

Example 11

1-Benzyl-4-chloro-3-(2-furyl)pyrazolo[3,4-d]pyrimidine

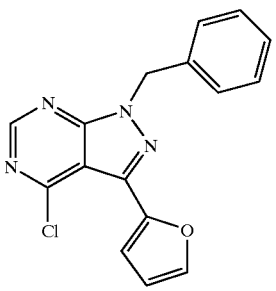

6.6 g of 1-benzyl-3-(2-furyl)-4-hydroxypyrazolo[3,4-d]pyrimidine are boiled for 12 h in 100 ml of $POCl_3$. The mixture is evaporated in vacuo, the residue is stirred with aqueous $K_2HPO_4$ solution and the mixture is extracted with ethyl acetate. After drying using $Na_2SO_4$ and concentrating in a rotary evaporator, 7.47 g of a solid are obtained which can be reacted directly for the next stage ($R_f$=0.8, $SiO_2$, toluene/ethyl acetate=1:1).

Example 12

1-Benzyl-3-(2-furyl)pyrazolo[3,4-d]pyrimidine

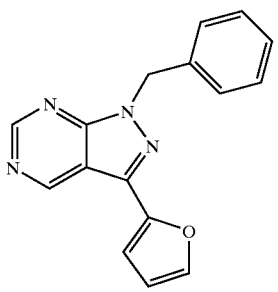

5.81g of 1-benzyl-4-chloro-3-(2-furyl)pyrazolo[3,4-d]pyrimidine are dissolved in 450 ml of dioxane and hydrogenated in the Parr apparatus at a hydrogen pressure of 3 bar for 5 h using 4 g of 20% $Pd(OH)_2$ on carbon after addition of 2.61 ml of triethylamine. After filtration through kieselguhr, evaporation and chromatography, 2.26 g of yellowish crystals are obtained (m.p.=106° C., $R_f$=0.2 toluene/ethyl acetate=4:1).

Example 13

1-Benzyl-3-(5-hydroxymethyl-2-furyl)-1-H-pyrazolo[3,4-b]pyridine

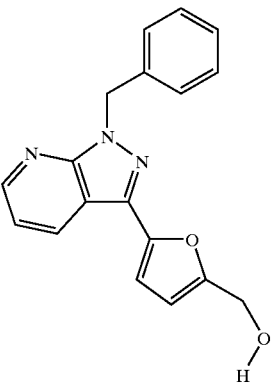

2.69 g (10 mmol) of 5-amino-1-benzyl-3-(5-hydroxymethyl-2-furyl)pyrazole and 1.4 g of malonaldehyde hydrate sodium salt are stirred at 100° C. for 30 min in 100 ml of dioxane and slowly treated with 1.9 ml of trifluoroacetic acid during the course of 5.5 hours. The mixture is evaporated in vacuo, the residue is taken up in ethyl acetate, the mixture is extracted by shaking with $K_2HPO_4$ solution, and the organic phase is dried using $Na_2SO_4$ and concentrated in vacuo in a rotary evaporator. The residue is chromatographed on silica gel. 200 mg (6.6% of theory) of crystals having a melting point of 104° C. are obtained.

The compounds mentioned in Table 3 are prepared in analogy to the abovementioned procedures:

TABLE 3

| Ex. No. | $R^{29}$ | $R^1$ | $R^{30}$ | $R^{31}$ | $R^{32}$ | m.p. [° C.] | $R_f$ | Yield (% of theory) |
|---|---|---|---|---|---|---|---|---|
| 14 | F | furyl-CH₂OH | H | H | H | 115 | 0.6 (EA) | 1.1 |
| 15 | F | furyl | H | H | H | 45 | 0.69 (T1E1) | 68 |
| 16 | F | pyrimidinyl | H | H | H | 163 | 0.33 (T1E1) | 11 |

TABLE 3-continued

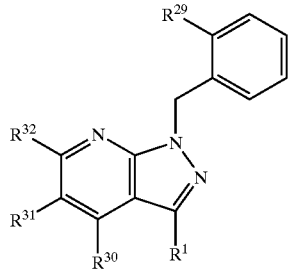

| Ex. No. | R29 | R1 | R30 | R31 | R32 | m.p. [° C.] | $R_f$ | Yield (% of theory) |
|---|---|---|---|---|---|---|---|---|
| 17 | F | 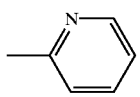 | H | H | H | 71 | 0.65 (T1E1) | 41 |
| 18 | H | 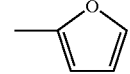 | Me | Me | Me | 115 | 0.84 (T1E1) | 71 |
| 19 | H | 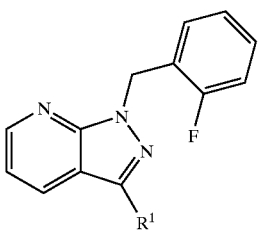 | Me | H | Me | 78 | 0.77 (T1E1) | 71 |

Example 20

3-(4,5-Dimethylpyrimidin-2-yl)-1-(2-fluorobenzyl)pyrazolo[3,4-b]pyrimidine

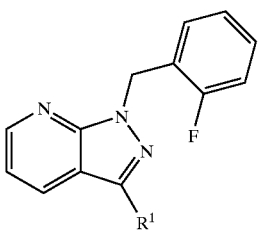

1.4 g (3.59 mmol) of 1-(2-fluorobenzyl)-3-trimethylstannylpyrazolo[3,4-b]pyrimidine are boiled overnight in toluene under argon with 0.51 g (3.58 mmol) of 2-chloro-4,5-dimethylpyrimidine and 0.2 g (0.28 mmol) of bis(triphenylphosphine)dichloropalladium. 3 g of silica gel are added and the solvent is evaporated in vacuo. The residue is then chromatographed on silica gel and eluted with a toluene/ethyl acetate mixture. 0.34 g (28.4% of theory) of the title compound having an m.p. of 167° C. and an $R_f$ of 0.08 (SiO$_2$, T4E) is obtained.

The example shown in Table 4 was prepared in an analogous manner.

TABLE 4

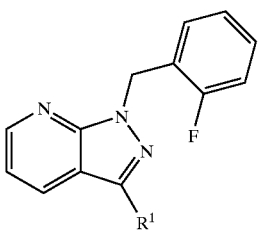

| Ex. No. | R1 |
|---|---|
| 21 | 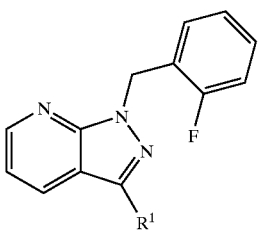 |

Example 22

1-Benzyl-3-(5-formyl-2-furyl)pyrazolo[3,4-d]pyrimidine

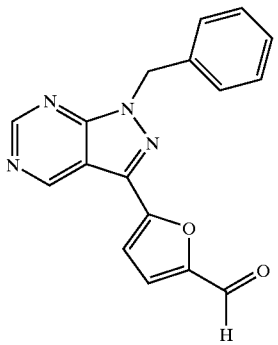

0.74 ml of $POCl_3$ is added at 0° C. to 0.64 ml of DMF. The solidified mixture is allowed to come to room temperature and 14 ml of 1,2-dichloroethane are added. A solution of 2 g of 1-benzyl-3-(2-furyl)pyrazolo[3,4-d]pyrimidine ($R_f$= 0.45, $SiO_2$, toluene/ethyl acetate=1:1) in 14 ml of 1,2-dichloroethane is added dropwise at 15° C. to this solution and it is then warmed to 80° C. After 4 h, the entire batch is added dropwise to further Vilsmeier reagent, which was prepared from 1.5 ml of $POCl_3$ and 1.3 ml of DMF, and stirred at 80° C. for 24 h. The mixture is then added to a 50% aqueous solution of $K_2HPO_4$ and briefly heated to 75° C. with stirring. After extraction with ethyl acetate, drying of the organic phase, concentration in a rotary evaporator and chromatography on $SiO_2$, 0.6 g (27% of theory) of an oil is obtained ($R_f$=0.3, $SiO_2$, toluene/ethyl acetate=1:1).

The examples from Table 5 are prepared in analogy to the abovementioned procedures.

TABLE 5

| Ex. No. | Structure | (° C.) | Yield (% of theory) | $R_f$ |
|---|---|---|---|---|
| 23 | 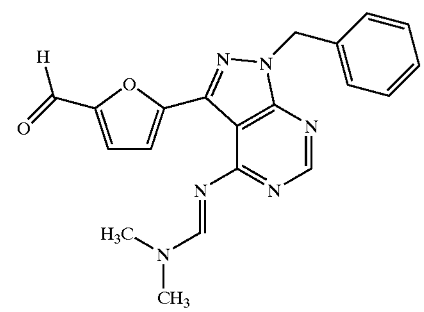 | 203 | 56.1 | 0.17 (EA) |
| 24 | 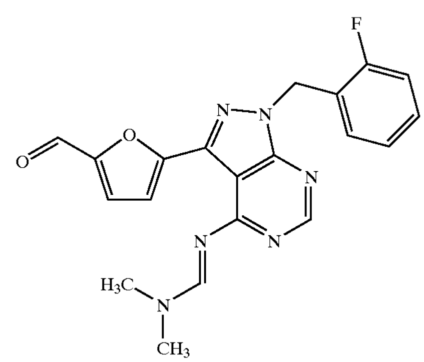 | 220 | 80,6 | 0.23 (EA) |
| 25 | 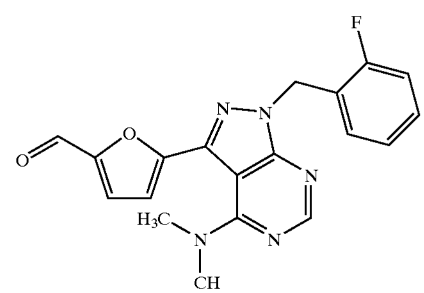 | 205 | 100 | 0.61 (EA) |

TABLE 5-continued

| Ex. No. | Structure | (° C.) | Yield (% of theory) | $R_f$ |
|---|---|---|---|---|
| 26 | 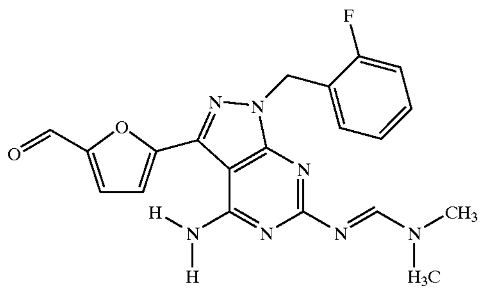 | 225 | 22.1 | 0.74 (T/E = 2:1) |
| 27 | 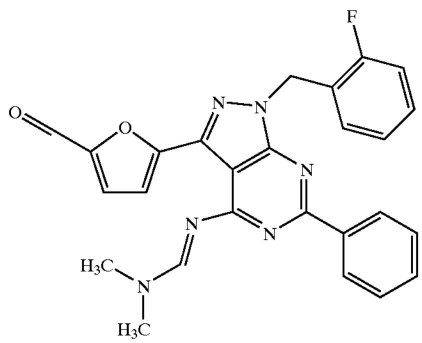 | 220 | 75 | 0.34 (T1E1) |
| 28 | 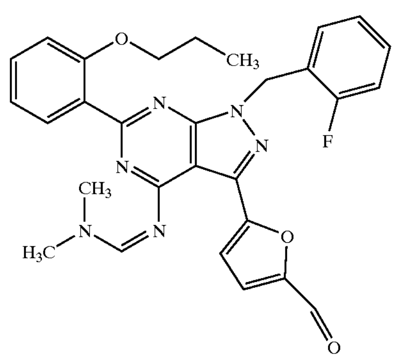 | 157 | 79 | 0.44 (T1E1) |
| 29 | 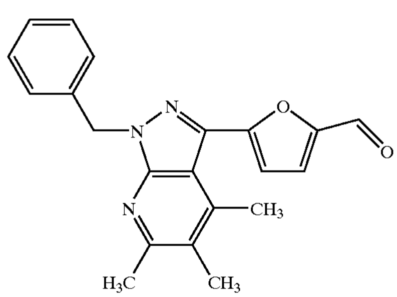 | 118 | 13.09 | 0.49 (T4:E1) |

TABLE 5-continued

| Ex. No. | Structure | (° C.) | Yield (% of theory) | $R_f$ |
|---|---|---|---|---|
| 30 | 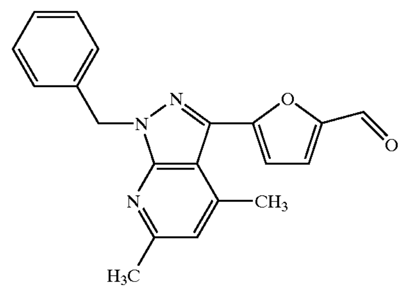 | 125 | 27.56 | 0.46 (T4:E1) |
| 31 | 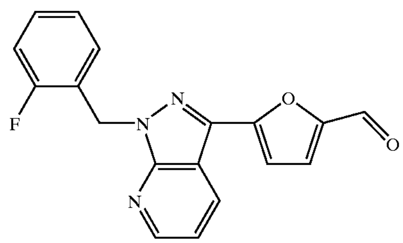 | 123 | 93 | 0.63 (T1:E1) |
| 32 | 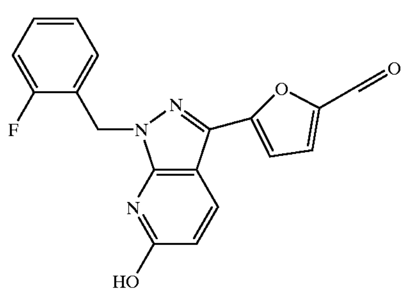 | 265 | 97 | 0.49 (T1:E1) |

Example 33

1-Benzyl-3-(5-hydroxymethyl-2-furyl)pyrazolo[3,4-d]pyrimidine

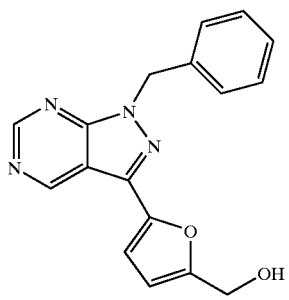

0.6 g (1.97 mmol) of 1-benzyl-3-(5-formyl-2-furyl)pyrazolo[3,4-d]pyrimidine ($R_f$=0.65, SiO$_2$, ethyl acetate) is treated with 60 mg of NaBH$_4$ with good stirring in 20 ml of 1-propanol at room temperature. After 15 min, 50 ml of water and 2.5 ml of glacial acetic acid are added. After partially concentrating in a rotary evaporator, the mixture is extracted with ethyl acetate, and the extract is dried and concentrated in a rotary evaporator after addition of toluene. After chromatography on SiO$_2$, 74.8 mg (12.4% of theory) of product are obtained (m.p. 165° C., $R_f$=0.43, SiO$_2$, ethyl acetate).

The compounds shown in Table 6 are prepared in analogy to the procedure of Example 33:

TABLE 6

| Ex. No. | Structure | m.p. [° C.] | Yield (% of theory) | $R_f$ |
|---|---|---|---|---|
| 34 | 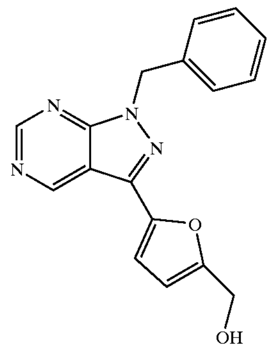 | 165 | 43.5 | 0.37 (EA) |
| 35 | 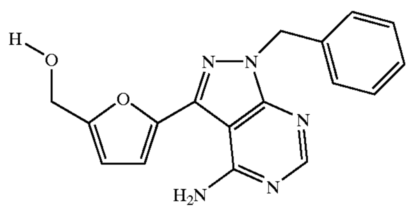 | 213 | 60 | 0.15 (EA) |
| 36 | 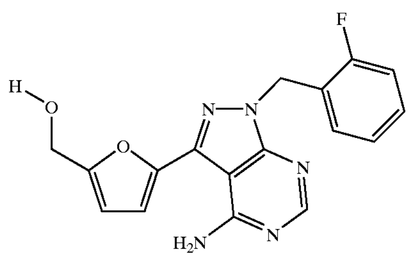 | 207 | 63 | 0.21 (EA) |
| 37 | 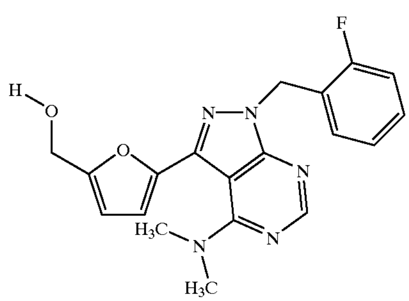 | 94 | 30 | 0.45 (EA) |
| 38 | 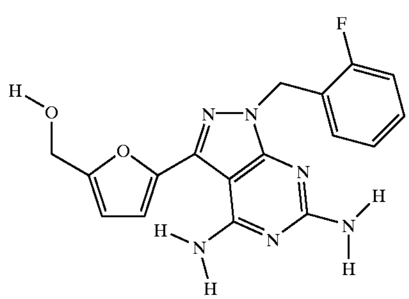 | 205 | 27.6 | 0.11 (EA) |

TABLE 6-continued

| Ex. No. | Structure | m.p. [° C.] | Yield (% of theory) | R$_f$ |
|---|---|---|---|---|
| 39 | 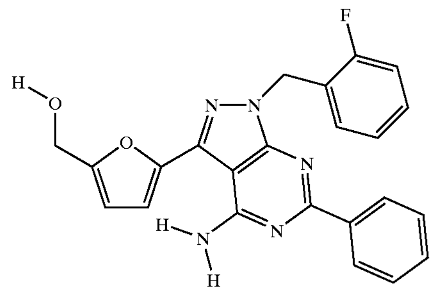 | 225 | 23.5 | 0.29 (T1E1) |
| 40 | 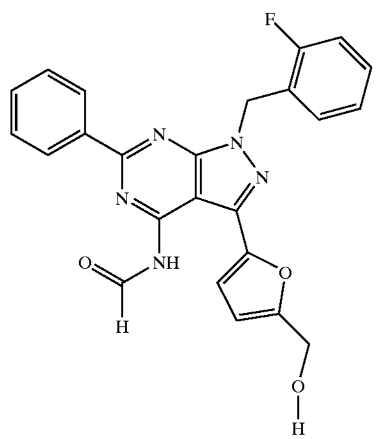 | 189 | 23 | 0.43 (T1E1) |
| 41 | 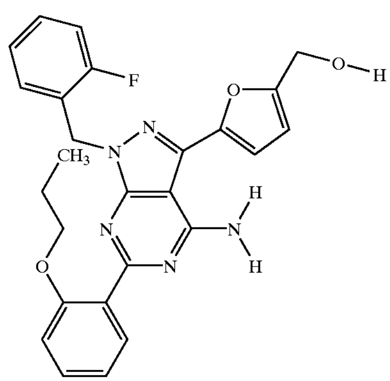 | | | |
| 42 | 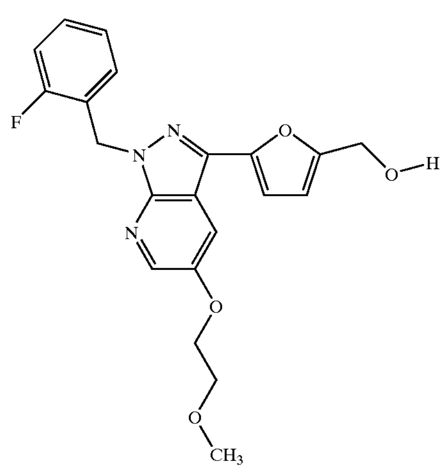 | 106 | 15.46 | 0.25 (T1E1) |

TABLE 6-continued

| Ex. No. | Structure | m.p. [° C.] | Yield (% of theory) | $R_f$ |
|---|---|---|---|---|
| 43 | 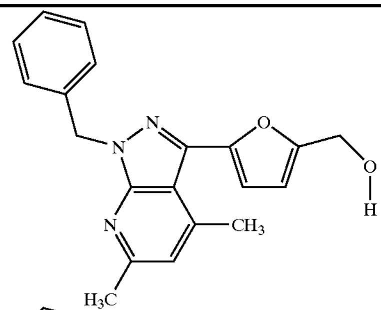 | 155 | 81.73 | 0.48 (T1E1) |
| 44 | 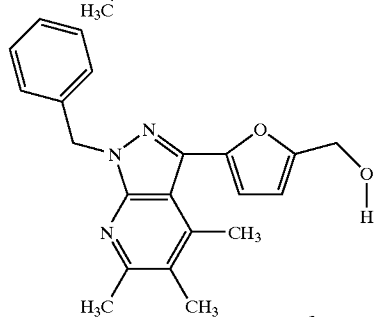 | 180 | 72.08 | 0.53 (T1E1) |
| 45 | 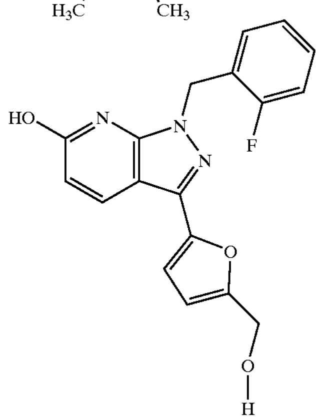 | | | 0.21 (T1E1) |

Example 46

Preparation of 1-(2-Fluorobenzyl)-3-[5-(piperidine-1-sulphinyl)furan-2-yl]-1H-pyrazolo-[3,4-b]pyridine

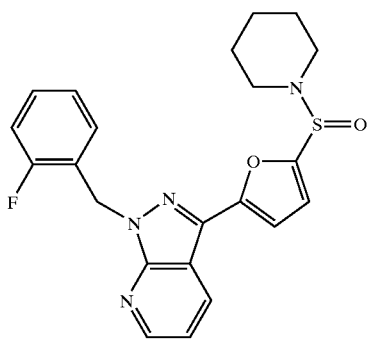

a) Preparation of 1-(2-Fluorobenzyl)-3-[5chlorosulphinylfuran2-yl]pyrazolo[3,4-b]-pyridine

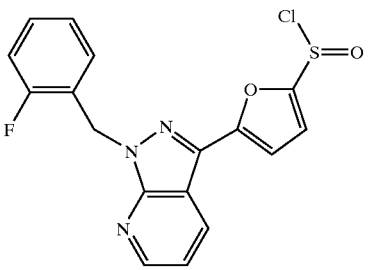

0.85 g (2.86 mmol) of 1-(2-fluorobenzyl)-3-(2-furyl)pyrazolo[3,4-b]pyridine is stirred with 20 ml of thionyl chloride for 25 min at 70° C. The batch is then evaporated in vacuo and reacted further in crude form.

b) The above batch is taken up in 30 ml of dioxane, treated with 0.6 ml (about 6 mmol) of piperidine, vigorously shaken and allowed to stand overnight. It is added to water and the mixture is extracted by shaking with ethyl acetate. After drying the organic phase using Na₂SO₄, it is evaporated and the residue is chromatographed on silica gel using a toluene/ethyl acetate gradient. 0.49 g (40% of theory) of a brown, clear viscous syrup is obtained (R$_f$ (SiO₂; T1E1) 0.36).

The compounds shown in Table 7 are prepared in analogy to the abovementioned procedures and that of Example 46.

Example 67 is prepared in analogy to the procedure of Example 20.

TABLE 7

| Ex. No. | Structure | m.p. (° C.) | Yield (% of theory) | R$_f$ |
|---|---|---|---|---|
| 47 | 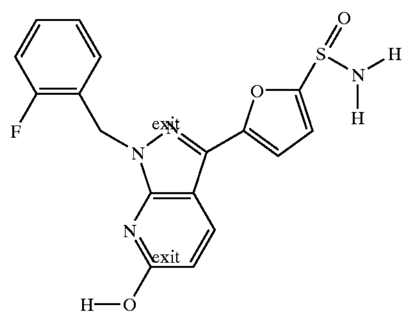 | 29.34 | | 0.37 EA |
| 48 | 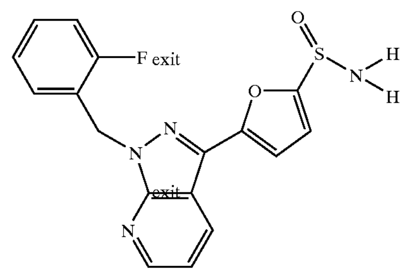 | 8.23 | | 0.12 (T1E1) |
| 49 | 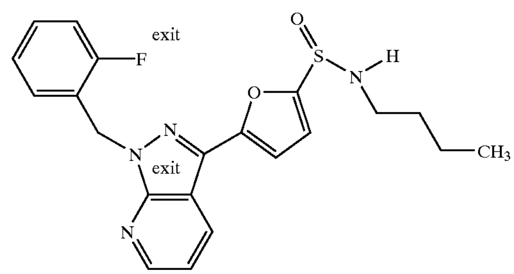 | oil | 10 | 0.37 (T1E1) |
| 50 | 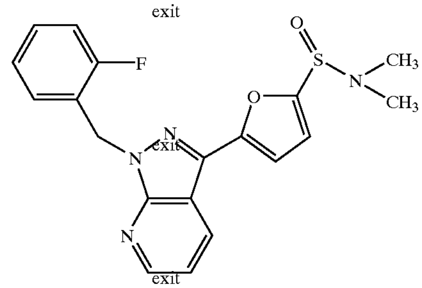 | 107 | 37 | 0.28 (T1E1) |
| 51 | 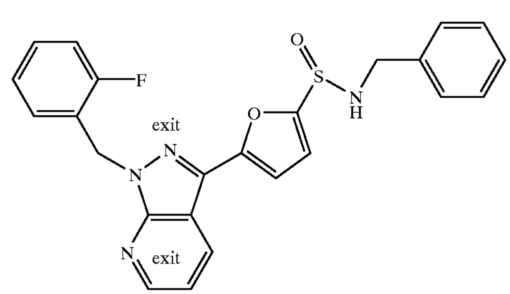 | 126 | 27 | 0.43 (T1E1) |

TABLE 7-continued

| Ex. No. | Structure | m.p. (° C.) | Yield (% of theory) | R$_f$ |
|---|---|---|---|---|
| 52 | 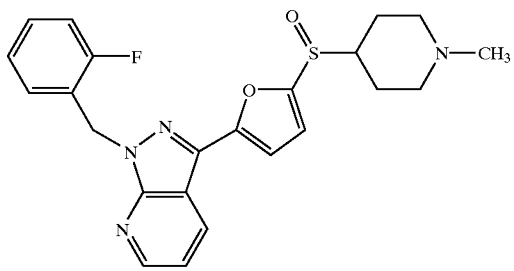 | 279 | 77 | 0.16 (EA/EtOH = 1:1) |
| 53 | 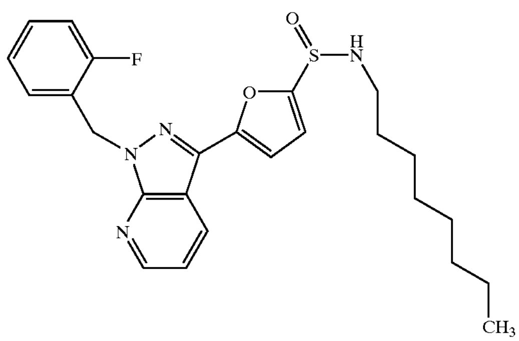 | 69 | 56 | 0.49 (T1E1) |
| 54 | 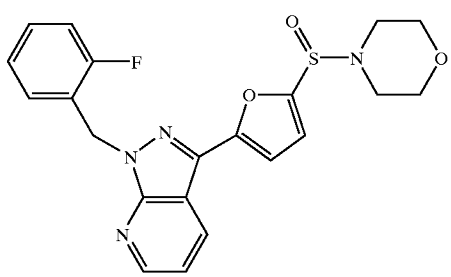 | 122 | 34 | 0.31 (T1:E1) |
| 55 | 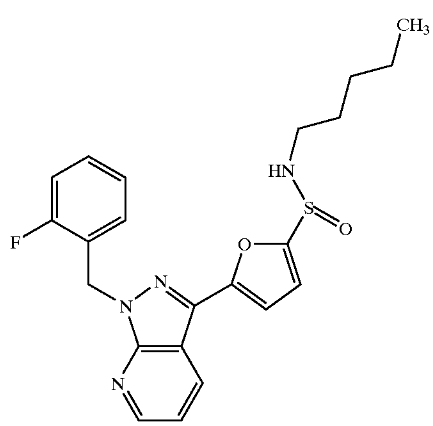 | oil | 4.2 | 0.37 (T1E1) |

TABLE 7-continued

| Ex. No. | Structure | m.p. (° C.) | Yield (% of theory) | R_f |
|---|---|---|---|---|
| 56 | 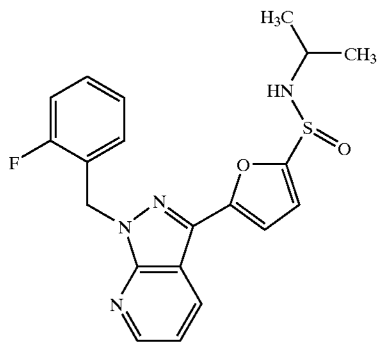 | 136 | 76 | 0.33 (T1E1) |
| 57 | 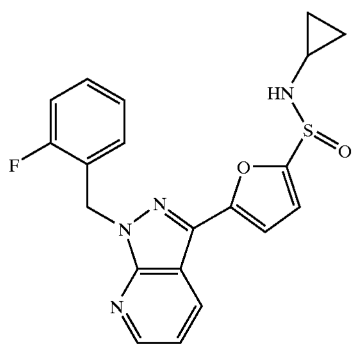 | 138 | 50 | 0.31 (T1E1) |
| 58 | 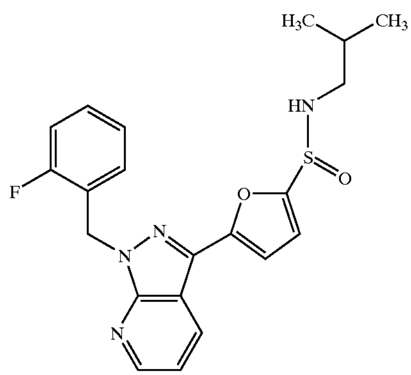 | 109 | 59 | 0.38 (T1E1) |
| 59 | 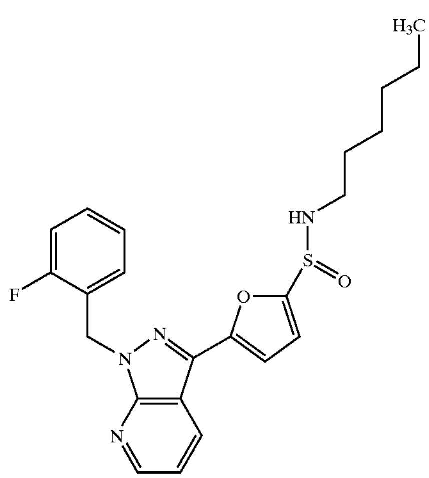 | 114 | 53 | 0.45 (T1E1) |

TABLE 7-continued

| Ex. No. | Structure | m.p. (° C.) | Yield (% of theory) | $R_f$ |
|---|---|---|---|---|
| 60 | 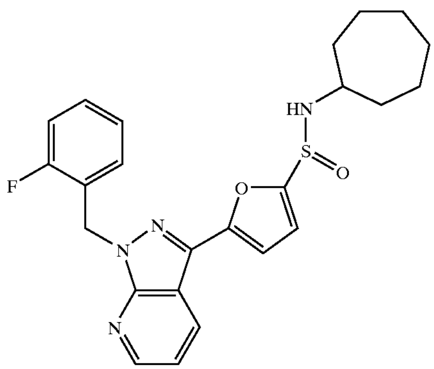 | 161 | 40 | 0.46 (T1E1) |
| 61 | 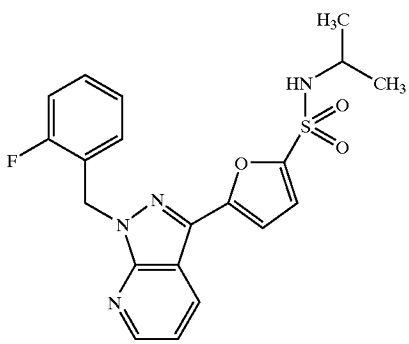 | 109 | 58 | 0.58 (T1E1) |
| 62 | 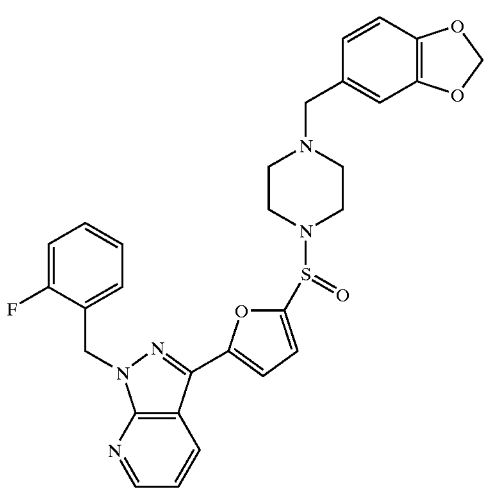 | oil | 65 | 0.17 (T1E1) |

TABLE 7-continued

| Ex. No. | Structure | m.p. (° C.) | Yield (% of theory) | $R_f$ |
|---|---|---|---|---|
| 63 | 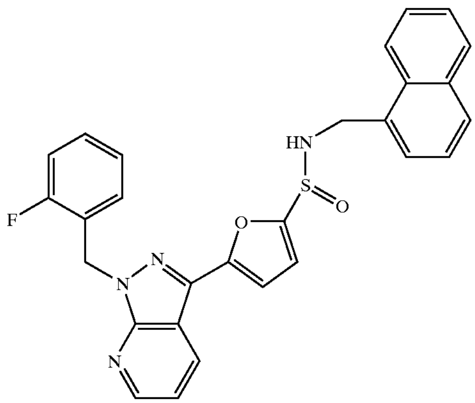 | 158 | 66 | 0.47 (T1E1) |
| 64 | 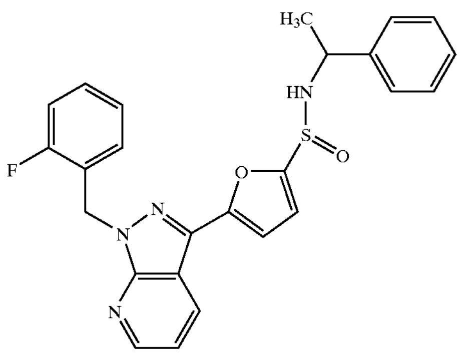 | 132 | 60 | 0.41 (T1E1) |
| 65 | 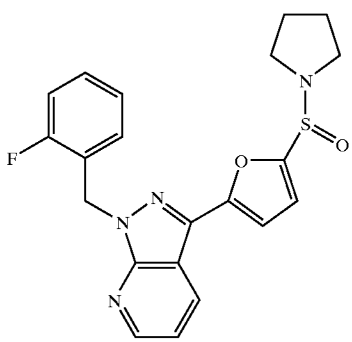 | 107 | 71 | 0.4 (T1E1) |
| 66 | 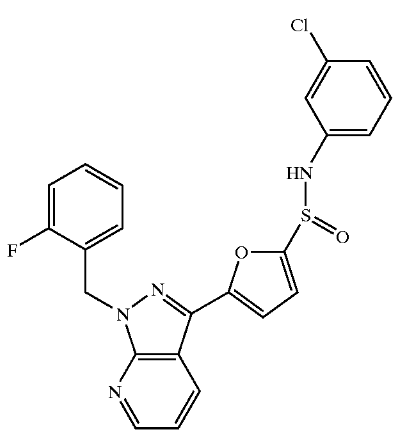 | 110 | 62 | 0.57 (T1E1) |

TABLE 7-continued

| Ex. No. | Structure | m.p. (° C.) | Yield (% of theory) | $R_f$ |
|---|---|---|---|---|
| 67 | 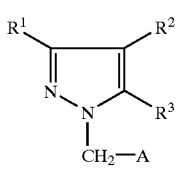 | 106 | 6 | 0.23 (hexane:EA 3:1) Al$_2$O$_3$ |

Example 68

1-(2-Fluorobenzyl)-3-(4-methyl-3-hydroxymethyloxazol-2-yl)pyrazolo[3,4b]pyridine

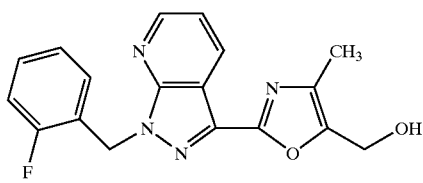

330 mg of 1-(2-fluorobenzyl)-3-( 1,1-dichlorobut-1-en-3-yl-amido)pyrazolo[3,4b]pyridine (0.84 mmol), 1.7 ml of NaOH 1N (1.68 mmol) and 3.3 ml of 1-methyl-2-pyrrolidone are stirred overnight at 50° C. then allowed to cool. The mixture is treated with water and ethyl acetate. The organic phase is separated, dried over Na$_2$SO$_4$ and concentrated. The mixture is dried in a high vacuum. The solid is then treated with cyclohexane/EA 2:1, crystals being formed. The crystals are filtered off with suction and stirred at RT with ether. An insoluble impurity is separated. The ethereal solution is concentrated and chromatographically purified, 52.1 mg (18%) of 1-(2-fluorobenzyl)-3-(4-methyl-3-hydroxymethyloxazol-2-yl)pyrazolo[3,4b]pyridine are obtained. M.p. 145° C. $R_f$: 0.074 (cyclohexane:EA 2:1). MS (ESI-POSITIVE): 339 (100, [M+H]$^+$).

Example 69

1-(2-Fluorobenzyl)-3-(4-ethyl-3'-hydroxymethyloxazol-2-yl)pyrazolo[3,4b]pyridine

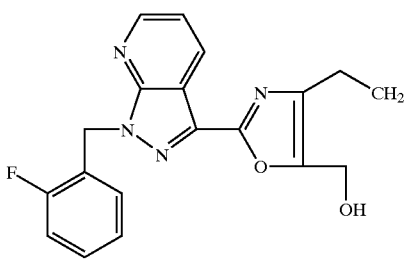

The compound is prepared in analogy to the procedure of Example 68. Yield (52% of theory), $R_f$ 0.33 (hexane:EA 1:1).

What is claimed is:

1. A substituted pyrazole compound of the formula (I):

$$\text{(I)}$$

(structure shown with R$^1$, R$^2$, R$^3$ substituents on pyrazole ring, N—CH$_2$—A)

in which

R$^1$ represents pyrimidinyl, is optionally substituted by 1 to 3 substituents independently selected from the group consisting of amino, azido, formyl, mercaptyl, carboxyl, hydroxyl, straight-chain or branched acyl having up to 6 carbon atoms, straight-chain or branched alkoxy having up to 6 carbon atoms, straight-chain or branched alkylthio having up to 6 carbon atoms, straight-chain or branched alkoxycarbonyl having up to 6 carbon atoms, nitro, cyano, halogen, phenyl, and alkyl having up to 6 carbon atoms, which alkyl is optionally substituted by hydroxyl, amino, azido, carboxyl, straight-chain or branched acyl having up to 5 carbon atoms, straight-chain or branched alkoxy having up to 5 carbon atoms, straight-chain or branched alkoxycarbonyl having up to 5 carbon atoms, straight-chain or branched acylamino having up to 5 carbon atoms, or a radical of the formula —OR$^4$;

in which

R$^4$ represents straight-chain or branched acyl having up to 5 carbon atoms, or a group of the formula —SiR$^5$R$^6$R$^7$;

in which

R$^5$, R$^6$ and R$^7$ independently represent aryl having 6 to 10 carbon atoms or alkyl having up to 6 carbon atoms; or the pyrimidinyl is substituted by a radical of the formula:

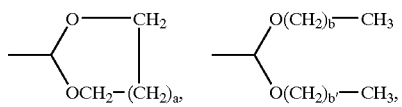

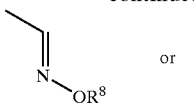
or

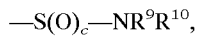

—S(O)$_c$—NR$^9$R$^{10}$,
in which
a, b and b' independently represent a number 0, 1, 2 or 3;
R$^8$ represents hydrogen or straight-chain or branched alkyl having up to 4 carbon atoms;
c represents a number 1 or 2; and
R$^9$ and R$^{10}$ independently represent hydrogen, straight-chain or branched alkyl having up to 10 carbon atoms, which alkyl can be optionally substituted by cycloalkyl having 3 to 8 carbon atoms or by optionally halogen substituted aryl having 6 to 10 carbon atoms, aryl having 6 to 10 carbon atoms, which aryl is optionally substituted by halogen, or cycloalkyl having 3 to 7 carbon atoms;

R$^2$ and R$^3$, together with the carbon atoms to which they are attached and the double bond joining said carbon atoms, form a pyridinyl ring, which is optionally substituted by 1 to 3 substituents independently selected from the group consisting. of formyl, carboxyl, hydroxyl, mercaptyl, straight-chain or branched acyl having up to 6 carbon atoms, straight-chain or branched alkylthio having up to 6 carbon atoms, straight-chain or branched alkoxy having up to 4 carbon atoms, straight-chain or branched alkoxycarbonyl having up to 6 carbon atoms, nitro, cyano, azido, halogen, straight-chain or branched alkyl having up to 6 carbon atoms, or straight-chain or branched alkoxy having up to 6 carbon atoms, which allyl or alkoxy is optionally substituted by hydroxyl, amino, carboxyl, straight-chain or branched acyl having up to 5 carbon atoms, straight-chain or branched alkoxy having up to 5 carbon atoms, or straight-chain or branched alkoxycarbonyl having up to 5 carbon atoms; or the pyridinyl is optionally substituted by a group of the formula —NR$^{12}$R$^{13}$ or —S(O)$_c$NR$^{9'}$R$^{10'}$;
in which
R$^{12}$ and R$^{13}$ independently represent hydrogen or straight-chain or branched alkyl having up to 6 carbon atoms; or
R$^{12}$ represents hydrogen; and
R$^{13}$ represents formyl;
c' represents a number 1 or 2; and
R$^{9'}$ and R$^{10'}$ independently represent hydrogen, straight-chain or branched alkyl having up to 10 carbon atoms, which alkyl can be optionally substituted by cycloalkyl having 3 to 8 carbon atoms or by optionally halogen substituted aryl having 6 to 10 carbon atoms, aryl having 6 to 10 carbon atoms, which aryl is optionally substituted by halogen, or cycloalkyl having 3 to 7 carbon atoms; or
the pyridinyl is optionally substituted by phenyl, which phenyl is optionally substituted by 1 or 2 substituents independently selected from the group consisting of halogen, straight-chain or branched alkyl having up to 6 carbon atoms, and straight-chain or branched alkoxy having up to 6 carbon atoms; and/or
the pyridinyl is optionally substituted by a group of the formula —N=CH—NR$^{14}$R$^{15}$;

in which
R$^{14}$ and R$^{15}$ independently represent hydrogen, phenyl or straight-chain or branched alkyl having up to 6 carbon atoms;

A represents phenyl, which is optionally substituted by 1 to 3 substituents independently selected from the group consisting of amino, mercaptyl, hydroxyl, formyl, carboxyl, straight-chain or branched acyl having up to 6 carbon atoms, straight-chain or branched alkylthio having up to 6 carbon atoms, straight-chain or branched alkyloxyacyl having up to 6 carbon atoms, straight-chain or branched alkoxy having up to 6 carbon atoms, straight-chain or branched aloxycarbonyl having up to 6 carbon atoms, nitro, cyano, trifluoromethyl, azido, halogen, phenyl, or straight-chain or branched alkyl having up to 6 carbon atoms, which alkyl is optionally substituted by hydroxyl, carboxyl, straight-chain or branched acyl having up to 5 carbon atoms, straight-chain or branched alkoxy having up to 5 carbon atoms, or straight-chain or branched alkoxycarbonyl having up to 5 carbon atoms; or the phenyl group A is optionally substituted by a group of the formula —(CO)$_d$—NR$^{16}$R$^{17}$;
in which
d represents a number 0 or 1; and
R$^{16}$ and R$^{17}$ independently represent hydrogen, phenyl, benzyl, straight-chain or branched alkyl having up to 5 carbon atoms, or straight-chain or branched acyl having up to 5 carbon atoms;

and a purified stereoisomes thereof or a salt thereof.

2. The pyrazole compound according to claim 1, in which
R$^1$ represents pyrimidinyl, is optionally substituted by 1 to 3 substituents independently selected from the group consisting of amino, formyl, mercaptyl, carboxyl, hydroxyl, straight-chain or branched acyl having up to 6 carbon atoms, straight-chain or branched alkoxy having up to 6 carbon atoms, straight-chain or branched alkylthio having up to 6 carbon atoms, straight-chain or branched alkoxycarbonyl having up to 6 carbon atoms, nitro, cyano, azido, fluorine, chlorine, bromine, phenyl, and alkyl having up to 5 carbon atoms, which alkyl is optionally substituted by hydroxyl, amino, azido, carboxyl, straight-chain or branched acyl having up to 4 carbon atoms, straight-chain or branched alkoxy having up to 4 carbon atoms, straight-chain or branched alkoxycarbonyl having up to 4 carbon atoms, straight-chain or branched acylamino having up to 4 carbon atoms, or a radical of the formula —OR$^4$;
in which
R$^4$ represents straight-chain or branched acyl having up to 4 carbon atoms; or
the pyrimidinyl is substituted by a radical of the formula:

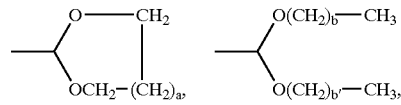

or

—S(O)$_c$—NR$^9$R$^{10}$,
in which
a, b and b' independently represent a number 0, 1, 2 or 3;
R$^8$ represents hydrogen or straight-chain or branched alkyl having up to 3 carbon atoms;
c represents a number 1 or 2; and
R$^9$ and R$^{10}$ independently represent hydrogen, straight-chain or branched alkyl having up to 9 carbon atoms, which alkyl can be optionally substituted by cyclopropyl, cyclobutyl, cyclopentyl, cyclohexyl, cycloheptyl, naphthyl or phenyl, which naphthyl or phenyl is optionally substituted by fluorine or chlorine, or represent phenyl or naphthyl, each of which phenyl or naphthyl is optionally substituted by fluorine or chlorine, or represent cyclopropyl, cyclobutyl, cyclopentyl, cyclohexyl or cycloheptyl;

R$^2$ and R$^3$, together with the carbon atoms to which they are attached and the double bond joining said carbon atoms, form a pyridinyl ring, which is optionally substituted by 1 to 3 substituents independently selected from the group consisting of formyl, carboxyl, hydroxyl, mercaptyl, straight-chain or branched acyl having up to 5 carbon atoms, straight-chain or branched alkylthio having up to 5 carbon atoms, straight-chain or branched alkoxycarbonyl having up to 5 carbon atoms, nitro, cyano, azido, fluorine, chlorine, bromine, straight-chain or branched alkyl having up to 5 carbon atoms, or straight-chain or branched alkoxy having up to 5 carbon atoms, which alkyl or alkoxy is optionally substituted by hydroxyl, amino, carboxyl, straight-chain or branched acyl having up to 4 carbon atoms, straight-chain or branched alkoxy having up to 4 carbon atoms, or straight-chain or branched alkoxycarbonyl having up to 4 carbon atoms; or the pyridinyl is optionally substituted by a group of the formula —NR$^{12}$R$^{13}$ or —S(O)$_c$NR$^{9'}$R$^{10'}$;
in which
R$^{12}$ and R$^{13}$ independently represent hydrogen or straight-chain or branched alkyl having up to 4 carbon atoms; or
R$^{12}$ represents hydrogen; and
R$^{13}$ represents formyl;
c' represents a number 1 or 2; and
R$^{9'}$ and R$^{10'}$ independently represent hydrogen, straight-chain or branched alkyl having up to 9 carbon atoms, which alkyl can be optionally substituted by cyclopropyl, cyclobutyl, cyclopentyl, cyclohexyl, cycloheptyl, naphthyl or phenyl, which naphthyl or phenyl is optionally substituted by fluorine or chlorine, or represent phenyl or naphthyl, each of which phenyl or naphthyl is optionally substituted by fluorine or chlorine, or represent cyclopropyl, cyclobutyl, cyclopentyl, cyclohexyl or cycloheptyl; or the pyridinyl is optionally substituted by phenyl, which phenyl is optionally substituted by fluorine, chlorine, bromine, straight-chain or branched alkyl having up to 4 carbon atoms, or straight-chain or branched alkoxy having up to 4 carbon atoms; or the pyridinyl is optionally substituted by a group of the formula —N=CH—NR$^{14}$R$^{15}$;
in which
R$^{14}$ and R$^{15}$ independently represent hydrogen or straight-chain or branched alkyl having up to 4 carbon atoms;

A represents phenyl, which is optionally substituted by 1 to 2 substituents independently selected from the group consisting of hydroxyl, formyl, carboxyl, straight-chain or branched acyl having up to 4 carbon atoms, straight-chain or branched alkylthio having up to 4 carbon atoms, straight-chain or branched alkyloxyacyl having up to 4 carbon atoms, straight-chain or branched alkoxy having up to 4 carbon atoms, straight-chain or branched alkoxycarbonyl having up to 4 carbon atoms, fluorine, chlorine, bromine, nitro, cyano, trifluoromethyl, or straight-chain or branched alkyl having up to 4 carbon atoms, which alkyl is optionally substituted by hydroxyl, carboxyl, straight-chain or branched acyl having up to 4 carbon atoms, straight-chain or branched alkoxy having up to 4 carbon atoms, or straight-chain or branched alkoxycarbonyl having up to 4 carbon atoms; or the phenyl group A is optionally substituted by a group of the formula —(CO)$_d$—NR$^{16}$R$^{17}$;
in which
d represents a number 0 or 1; and
R$^{16}$ and R$^{17}$ independently represent hydrogen, phenyl, benzyl, straight-chain or branched alkyl having up to 4 carbon atoms, or straight-chain or branched acyl having up to 4 carbon atoms;

said pyrazole compound optionally being in the form of a purified stereoisomer thereof;
or a salt of said pyrazole compound.

3. The pyrazole compound according to claim 1, in which

R$^1$ represents pyrimidinyl, is optionally substituted by 1 to 3 substituents independently selected from the group consisting of formyl, fluorine, chlorine, amino, mercaptyl, cyano, straight-chain or branched acyl having up to 4 carbon atoms, straight-chain or branched alkoxy having up to 4 carbon atoms, straight-chain or branched alkylthio having up to 4 carbon atoms, straight-chain or branched alkoxycarbonyl having up to 4 carbon atoms, and alkyl having up to 4 carbon atoms, which alkyl is optionally substituted by hydroxyl, carboxyl, amino, azido, straight-chain or branched acyl having up to 3 carbon atoms, straight-chain or branched alkoxy having up to 3 carbon atoms, straight-chain or branched alkoxycarbonyl having up to 3 carbon atoms, straight-chain or branched acylamino having up to 3 carbon atoms; or the pyrimidinyl is substituted by a radical of the formula:

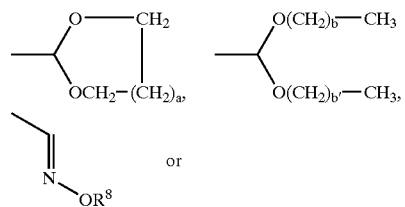

or
—S(O)$_c$—NR$^9$R$^{10}$,
in which
a, b and b' independently represent a number 0, 1 or 2;
R$^8$ represents hydrogen or methyl;
c represents a number 1 or 2; and
R$^9$ and R$^{10}$ independently represent hydrogen, straight-chain or branched alkyl having up to 9 carbon atoms, which alkyl can be optionally substituted by naphthyl or phenyl, which naphthyl or phenyl is optionally substituted by fluorine or chlorine, or represent phenyl or naphthyl, each of which phenyl or naphthyl is optionally substituted by fluorine or chlorine, or represent cyclopropyl or cycloheptyl;

$R^2$ and $R^3$, together with the carbon atoms to which they are attached and the double bond joining said carbon atoms, form a pyridinyl ring, which is optionally substituted by 1 to 3 substituents independently selected from the group consisting of formyl, carboxyl, hydroxyl, mercaptyl, straight-chain or branched acyl having up to 4 carbon atoms, straight-chain or branched alkoxy having up to 4 carbon atoms, straight-chain or branched alkylthio having up to 4 carbon atoms, straight-chain or branched alkoxycarbonyl having up to 4 carbon atoms, nitro, cyano, fluorine, chlorine, straight-chain or branched alkyl having up to 3 carbon atoms, or straight-chain or branched alkoxy having up to 3 carbon atoms, which alkyl or alkoxy is optionally substituted by hydroxyl, amino, carboxyl, straight-chain or branched acyl having up to 3 carbon atoms, straight-chain or branched alkoxy having up to 3 carbon atoms, or straight-chain or branched alkoxycarbonyl having up to 3 carbon atoms; or the pyridinyl is optionally substituted by amino, N,N-dimethylamino, —NH—CHO, or —N=CH—N(CH$_3$)$_2$ and/or by phenyl, which phenyl is optionally substituted by a radical of the formula —O—(CH$_2$)$_2$—CH$_3$;

A represents phenyl, which is optionally substituted by 1 to 2 substituents independently selected from the group consisting of formyl, carboxyl, straight-chain or branched acyl having up to 3 carbon atoms, straight-chain or branched alkylthio having up to 3 carbon atoms, straight-chain or branched alkyloxyacyl having up to 3 carbon atoms, straight-chain or branched alkoxy having up to 3 carbon atoms, straight-chain or branched alkoxycarbonyl having up to 3 carbon atoms, fluorine, chlorine, bromine, nitro, cyano, trifluoromethyl, or straight-chain or branched alkyl having up to 3 carbon atoms, which alkyl is optionally substituted by hydroxyl, carboxyl, straight-chain or branched acyl having up to 3 carbon atoms, straight-chain or branched alkoxy having up to 3 carbon atoms, or straight-chain or branched alkoxycarbonyl having up to 3 carbon atoms;

said pyrazole derivative optionally being in the form of a purified stereoisomer thereof; or a salt of said pyrazole compound.

4. A process for preparing the pyrazole derivative or salt thereof according to claim 1, said process comprising:

a) reacting a compound of the formula (II):

$$R^1—D \qquad (II)$$

in which
$R^1$ has the meaning given in claim 1; and
D represents a radical of the formula:

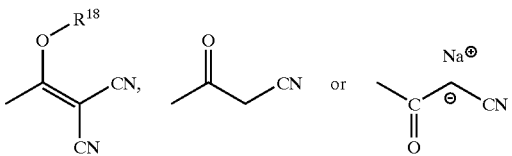

in which
$R^{18'}$ represents $C_{1-4}$-alkyl;
with a compound of the formula (III):

$$A—CH_2—NH—NH_2 \qquad (III)$$

in which
A has the meaning given in claim 1;
in an inert solvent, optionally in the presence of a base, to yield a compound of the formula (IV) or (IVa):

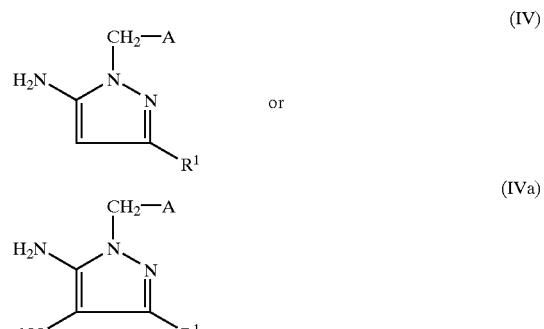

in which
A and $R^1$ have the meanings indicated above; and
b) cyclizing the compound of the formula (IVa) with a carboxylic acid, nitrile, formamide or guanidinium salt; or
c) cyclizing the compound of the formula (IV) with a 1,3-dicarbonyl derivative or a salt, tautomer, enol ether or enamine thereof, in the presence of an acid and, optionally, under microwaves.

5. A process for preparing the pyrazole compound or salt thereof according to claim 1, said process comprising:

a) reacting a compound of the formula (VII):

in which
A, $R^2$ and $R^3$ have the meaning given in claim 1; and
L represents a radical of the formula —SnR$^{19}$R$^{20}$R$^{21}$, ZnR$^{22}$, iodine, bromine or triflate;
in which
$R^{19}$, $R^{20}$ and $R^{21}$ independently represent straight-chain or branched alkyl having up to 4 carbon atoms; and
$R^{22}$ represents halogen;
with a compound of the formula (VII):

$$R^1—T \qquad (VIII)$$

in which $R^1$ has the meaning given in claim 1; and

T represents triflate or halogen if L represents —$SnR^{19}R^{20}R^{21}$ or $ZnR^{22}$; or T represents a radical of the formula —$SnR^{19'}R^{20'}R^{21'}$, $ZnR^{22'}$ or $BR^{23'}R^{24'}$ if L represents iodine, bromine or triflate;

in which $R^{19'}$, $R^{20'}$ and $R^{21'}$ independently represent straight-chain or branched alkyl having up to 4 carbon atoms;

$R^{22'}$ represents halogen; and $R^{23'}$ and $R^{24'}$ independently represent hydroxyl, aryloxy having 6 to 10 carbon atoms, straight-chain or branched alkyl having up to 5 carbon atoms, or straight-chain or branched alkoxy having up to 5 carbon atoms, or together $R^{23'}$ and $R^{24'}$ form a 5- or 6-membered carbocyclic ring;

in the presence of a palladium catalyst in an inert solvent, optionally, in the presence of a base.

6. A pharmaceutical composition comprising at least one pyrazole compound or salt thereof according to claim 1.

7. The pharmaceutical composition according to claim 6, which further comprises at least one organic nitrate or NO donor.

8. The pharmaceutical composition according to claim 6, which further comprises at least one compound which inhibits the degradation of cyclic guanosine monophosphate (cGMP).

9. A method of treating a cardiovascular disease, said method comprising administering to a patient in need thereof an effective amount therefor of at least one pyrazole compound or salt thereof according to claim 1.

10. A method of treating a thromboembolic disorder or ischaemia, said method comprising administering to a patient in need thereof an effective amount therefor of at least one pyrazole compound or salt thereof according to claim 1.

* * * * *

UNITED STATES PATENT AND TRADEMARK OFFICE
CERTIFICATE OF CORRECTION

PATENT NO.     : 6,451,805 B1
DATED          : September 17, 2002
INVENTOR(S)    : Alexander Straub et al.

It is certified that error appears in the above-identified patent and that said Letters Patent is hereby corrected as shown below:

<u>Column 59,</u>
Line 37, delete "allyl" and substitute -- alkyl --

Signed and Sealed this

Third Day of February, 2004

JON W. DUDAS
*Acting Director of the United States Patent and Trademark Office*